(12) United States Patent
Craighead et al.

(10) Patent No.: US 7,148,017 B1
(45) Date of Patent: Dec. 12, 2006

(54) HIGH SENSITIVITY MECHANICAL RESONANT SENSOR

(75) Inventors: Harold G. Craighead, Ithaca, NY (US); Bojan Ilic, Ithaca, NY (US); David Alan Czaplewski, Ithaca, NY (US); Robert H. Hall, Clarksville, MD (US)

(73) Assignee: Cornell Research Foundation, Inc., Ithaca, NY (US)

( * ) Notice: Subject to any disclaimer, the term of this patent is extended or adjusted under 35 U.S.C. 154(b) by 978 days.

(21) Appl. No.: 09/712,795

(22) Filed: Nov. 14, 2000

Related U.S. Application Data

(60) Provisional application No. 60/217,818, filed on Jul. 12, 2000.

(51) Int. Cl.
*G01N 33/53* (2006.01)

(52) U.S. Cl. ............... 435/7.1; 435/52.6; 435/7.32; 435/7.8; 435/808; 435/287.2; 435/7.2; 436/512; 436/525; 422/55; 422/56; 422/82.11; 422/119; 73/105; 250/306; 250/307

(58) Field of Classification Search .......... 435/6, 435/7.1, 7.2, 526, 7.32, 7.8, 808, 287.2; 536/120; 436/512, 525; 422/55, 56, 82.11, 119; 73/105; 250/306, 307

See application file for complete search history.

(56) References Cited

U.S. PATENT DOCUMENTS

| | | | |
|---|---|---|---|
| 4,242,096 A | 12/1980 | Oliveira et al. | ........... 23/230 B |
| 4,999,284 A | 3/1991 | Ward et al. | ............... 435/4 |
| 5,001,053 A | 3/1991 | Takahashi et al. | ........... 435/7.1 |
| 5,135,852 A | 8/1992 | Ebersole et al. | ............ 435/39 |
| 5,306,644 A | 4/1994 | Myerholtz et al. | .......... 436/149 |
| 5,541,057 A | 7/1996 | Bogart et al. | ................ 435/5 |
| 5,550,063 A | 8/1996 | Bogart | ....................... 436/518 |
| 5,656,809 A * | 8/1997 | Miyashita et al. | .......... 250/225 |
| 5,658,732 A | 8/1997 | Ebersole et al. | ............... 435/6 |
| 5,705,399 A | 1/1998 | Larue | ......................... 436/501 |
| 5,719,324 A | 2/1998 | Thundat et al. | ............ 73/24.01 |
| 5,756,279 A * | 5/1998 | Ebersole et al. | ................ 435/4 |
| 5,807,758 A | 9/1998 | Lee et al. | .................... 436/526 |
| 5,814,525 A | 9/1998 | Renschler et al. | .......... 436/524 |
| 5,945,280 A | 8/1999 | Fawcett et al. | ................ 435/5 |
| 6,016,686 A | 1/2000 | Thundat | .................... 73/23.2 |
| 6,124,765 A * | 9/2000 | Chan et al. | ............. 331/116 M |
| 6,203,983 B1* | 3/2001 | Quate et al. | ................... 435/6 |
| 6,436,647 B1* | 8/2002 | Quate et al. | ................... 435/6 |
| 2003/0154771 A1* | 8/2003 | de Charmoy Grey et al. | ........................ 73/53.01 |

OTHER PUBLICATIONS

Baselt, D.R.,et al.,"A High-Sensitivity Micromachined Biosensor", *Proc. IEEE, 85 (4)*, (1997),pp. 672-680.
Baselt, D.R.,et al.,"Biosensor based on force microscope technology", *J. Vac. Sci. Technol. B., 14 (2)*, (1996),pp. 789-793.
Carr, D.,et al.,"Fabrication of nanoelectromechanical systems in single crystal silicon using silicon on insulator substrates and electron beam litography", *J. Vac. Sci. Technol. B., 15(6)*, (1997),pp. 2760-2763.
Carr, D.,et al.,"Measurement of nanomechanical resonant structures in single-crystal silicon", *J. Vac. Sci. Technol. B, 16(6)*, (1998),pp. 3821-3824.
Fritz, J.,et al.,"Translating Biomolecular Recognition into Nanomechanics", *Science, 288*, (2000),pp. 316-318.
Ilic, B.,et al.,"Mechanical resonant immunospecific biological detector", *Applied Physics Letters, 77(3)*, (2000),pp. 450-452.
Ilic, B.,et al.,"Ultra-Sensitive Resonant Frequency Based Mass Detector", *Proc. Electrochem. Soc.*, (2000),1 page.
Kadar, Z.,"Integrated Resonant Magnetic Field Sensor", http://www.xs4all.nl/~kadzsol/thesis/ch2.chap2.html, Philosophical Dissertation, Chapter 2, "Design Considerations",(1997),21 p.
Lang, H.,et al.,"A Chemical sensor based on a micromechanical cantilever array for the identification of gases and vapors", *Appl. Phys. A, 66*, (1998),pp. S61-S64.

\* cited by examiner

*Primary Examiner*—Long V. Le
*Assistant Examiner*—Jacob Cheu
(74) *Attorney, Agent, or Firm*—Schwegman, Lundberg, Woessner & Kluth, P.A.

(57) ABSTRACT

A system and method for detecting mass based on a frequency differential of a resonating micromachined structure, such as a cantilever beam. A high aspect ratio cantilever beam is coated with an immobilized binding partner that couples to a predetermined cell or molecule. A first resonant frequency is determined for the cantilever having the immobilized binding partner. Upon exposure of the cantilever to a solution that binds with the binding partner, the mass of the cantilever beam increases. A second resonant frequency is determined and the differential resonant frequency provides the basis for detecting the target cell or molecule. The cantilever may be driven externally or by ambient noise. The frequency response of the beam can be determined optically using reflected light and two photodetectors or by interference using a single photodetector.

23 Claims, 18 Drawing Sheets

HIGH SENSITIVITY MECHANICAL RESONANT SENSOR

This application claims benefit of Provisional No. 60/217,818 filed Jul. 12, 2000.

GOVERNMENT FUNDING

The invention described herein was made with Government support by the Defense Advanced Research Projects Agency, through an Office of Naval Research grant number N00014-97-10-0779, and by the National Science Foundation, under contract number ECS-9876771. The United States Government has certain rights in the invention.

TECHNICAL FIELD OF THE INVENTION

The present invention relates generally to the field of chemical and biological sensors and, in particular, to a high sensitivity, mechanical resonant sensor for detecting the presence of chemical or biological material.

BACKGROUND

Science and industry have developed a need for the ability to accurately detect and measure very small quantities of chemical or biological material. Where it was once adequate to measure quantities in micrograms, today, many applications require the detection of a single cell, subcellular unit, or other small quantity of material, sometimes on the order of $10^{-15}$ grams.

For example, within the food industry, even small quantities of particular biological cells or toxins can be harmful or dangerous to mammals. One such well recognized harmful organism is *Escherichia coli* or *E. coli* bacteria. Popular media attention concerning the presence of *E. coli* in meat products, apple juice and alfalfa sprouts has heightened consumer sensitivities.

Sensors for detecting gasses using micromechanical cantilevers are discussed in *A Chemical Sensor Based on a Micromechanical Cantilever Array for the Identification of Gases and Vapors*, H. P. Lang (IBM Corporation, Saumerstrasse 4, 8803 Ruschlikon, Switzerland) et al., Applied Physics A 66, No. S, S61–S64 (1998) (hereinafter "Lang"). Lang discusses detecting static beam deflection upon exposure of the beam to gases and vapors and measuring resonance frequency shifts based on changes of beam mass due to absorption. Absorbent beams are exposed to a chemical vapor for a period of time (noted in one instance to be several hours) and measurements are taken before the chemicals have evaporated from the beam. Absorption is recognized as largely a result of Lennard-Jones potential, wherein at close distances, nearby molecules repel and at larger distances, the molecules are attracted to each other. In many cases, absorption of molecules onto a surface can be readily reversed by merely heating the system or exposing the system to a vacuum.

Biochemically induced surface stresses in a cantilever array are discussed in *Translating Biomolecular Recognition into Nanomechanics*, J. Fritz et al, Science, page 316–318, Vol. 288, Apr. 14, 2000 (hereinafter "Fritz"). Fritz discusses absolute deflection of a beam as it relates to ligand binding in a liquid environment.

Detecting mass differences using static deflection of a beam typically requires a more robust beam. In many cases, this means that the beam is dimensionally rather large or the material of which the beam is fabricated has a relatively high Young's Modulus of elasticity. Large beams or those having high Young's Modulus of elasticity can lack the sensitivity needed to detect small quantities of target substances. In addition, beams that acquire additional mass through the process of absorption often require lengthy exposure time to the target substance to accumulate a detectable amount.

For the reasons stated above, and for other reasons stated below which will become apparent to those skilled in the art upon reading and understanding the present specification, there is a need in the art for a highly sensitive detection system and method that permits the rapid detection of biological or chemical material.

SUMMARY

The above mentioned problems with sensors, and other problems, are addressed by the present invention and will be understood by reading and studying the following specification. A system is described for detecting an analyte. The system can include a light source, a resonating structure (such as a cantilever beam) and a photodiode. The beam has a rigid end and a free end that resonates under ambient conditions. The resonant frequency of the beam is a function of, inter alia, the mass on the beam. The photodiode generates an output signal based on light reflected from the apex of the beam. The photodiode output is a function of the frequency of vibration of the beam. At least one surface of the beam includes an immobilized binding partner. The binding partner is selected so as to bind with a particular analyte, or analytes, which in turn, increases the mass of the beam.

The processor can be coupled to the photodiode and the processor can execute programming to determine the mass of analyte bound to the binding partner. The processor can include a microprocessor or a spectrum analyzer coupled to the output signal. The binding partner can be immobilized on a particular region of the beam, such as, for example near one end of the beam. The beam can be fabricated of silicon nitride. A portion of the beam can be rigidly coupled to a support. The length of the beam may be in the range of 0.5 to 1000 μm. The beam can be adjusted to vibrate in an out of plane mode. The beam can operate in an atmosphere of thermal noise or it can operate in an atmosphere of air vibrations. The beam can be tailored to detect an analyte including a pathogen, a microorganism, a bacteria, a virus or a subunit thereof. The binding partner can include an antibody that binds to a particular analyte such as a cell, a cell fragment or subunit. The binding partner can include a cellular receptor that binds to a ligand. The analyte can be a ligand specific for a cellular receptor. The analyte can be a metallic ion, or organic molecule, and the binding partner can be a chelator that binds to the metallic ion, or organic molecule. The binding partner may include a deoxyribonucleic acid ("DNA") sequence and the analyte include a complementary DNA sequence that hybridizes thereto under the operational conditions of the sensor.

A method for detecting a pathogen is also described. The method can include providing a cantilever beam, optically determining a first resonant frequency for the beam, exposing the cantilever beam to a mixture suspected of containing the pathogen, optically determining a second resonant frequency for the beam, and determining a mass difference for the beam. The beam includes an immobilized binding partner for the pathogen on a surface thereof. The first resonant frequency is determined at a time when the beam is excited by ambient conditions and the second resonant frequency is determined at a time after the beam is exposed to the mixture. The mass difference is determined based on a difference between the first resonant frequency and the second resonant frequency.

The first resonant frequency can be determined by illuminating the beam using a laser light source and sensing light reflected by the beam using a photodiode. The ambient conditions can include thermal mechanical noise and ambient air vibrations. The cantilever beam can also be driven by a piezo electric oscillator. The binding partner can be immobilized by immersing the beam in a first liquid mixture of the binding partner for a pathogen, removing unbound pathogen or other components of the mixture, e.g., by rinsing with water and drying the beam in an inert atmosphere. The beam can be exposed by immersing the beam in a solution suspected of containing the pathogen, incubating the beam for a predetermined period of time, rinsing and drying the beam in an inert atmosphere. The beam can be exposed to a buffered aqueous solution. The pathogen can include a microorganism, microorganism fragment or subunit thereof. A second beam can also be prepared by immersing in a second solution suspected of containing a second pathogen. The beam can operate in a vacuum environment. The mechanical properties of the beam can be tailored to detect a mass difference in the range of attograms ($10^{-18}$ g) to micrograms ($10^{-6}$ g). The mechanical properties of the beam can be tailored to achieve a desired resonant frequency.

An array of analyte detectors is also disclosed. An array can include a plurality of cantilever beams, a plurality of immobilized binding partners and a sensor responsive to light reflected by a particular beam. Each beam resonates at a particular frequency under ambient conditions. Each beam has an immobilized binding partner on a surface. Each binding partner binds to a predetermined analyte. The sensor generates an output signal based on a resonant frequency of a particular beam.

At least some beams can be made of silicon nitride. A light source can be used to illuminate a beam. At least some beams in the array can have different, or heterogeneous, binding partners. At least some beams in the array can have the same, or homogeneous, binding partners.

A detector for an analyte is disclosed. The detector includes binding means, cantilever means, sensor means and processor means. The binding means are for binding with the analyte. The cantilever means are for resonating under ambient conditions. The binding means are immobilized on a portion of the cantilever means. The cantilever means resonates in a first mode at a first resonant frequency. The sensor means are for determining the first resonant frequency. The processor means are for determining a mass of the analyte based on a difference between the first resonant frequency and a second resonant frequency after exposure of the binding means to the analyte.

The cantilever means can vibrate in an out of plane mode. The cantilever means can include silicon nitride. The sensor can include a photodiode. The processor means can include a frequency analyzer. The binding means can be immobilized at a location near an unsupported end of the cantilever means. The cantilever means can be aligned substantially horizontally. The cantilever means can be encapsulated in a vacuum.

The system can include a cantilever beam driver in communication with the cantilever beam. The driver can vibrate the beam at a predetermined frequency and a sensor can monitor the amplitude of vibrations of the cantilever beam. The amplitude of vibrations will vary based on the mass of the analyte on the cantilever beam. Alternatively, the driver can vibrate the cantilever beam over a range of frequencies and a peak vibration amplitude of the beam corresponds to the resonant frequency of the beam.

DETAILED DESCRIPTION

The following detailed description refers to the accompanying drawings which form a part of the specification. The drawings show, and the detailed description describes, by way of illustration specific illustrative embodiments in which the invention may be practiced. These embodiments are described in sufficient detail to enable those skilled in the art to practice the invention. Other embodiments may be used and logical, mechanical, electrical and chemical changes may be made without departing from the scope of the present invention. The following detailed description is, therefore, not to be taken in a limiting sense.

Figure 1:
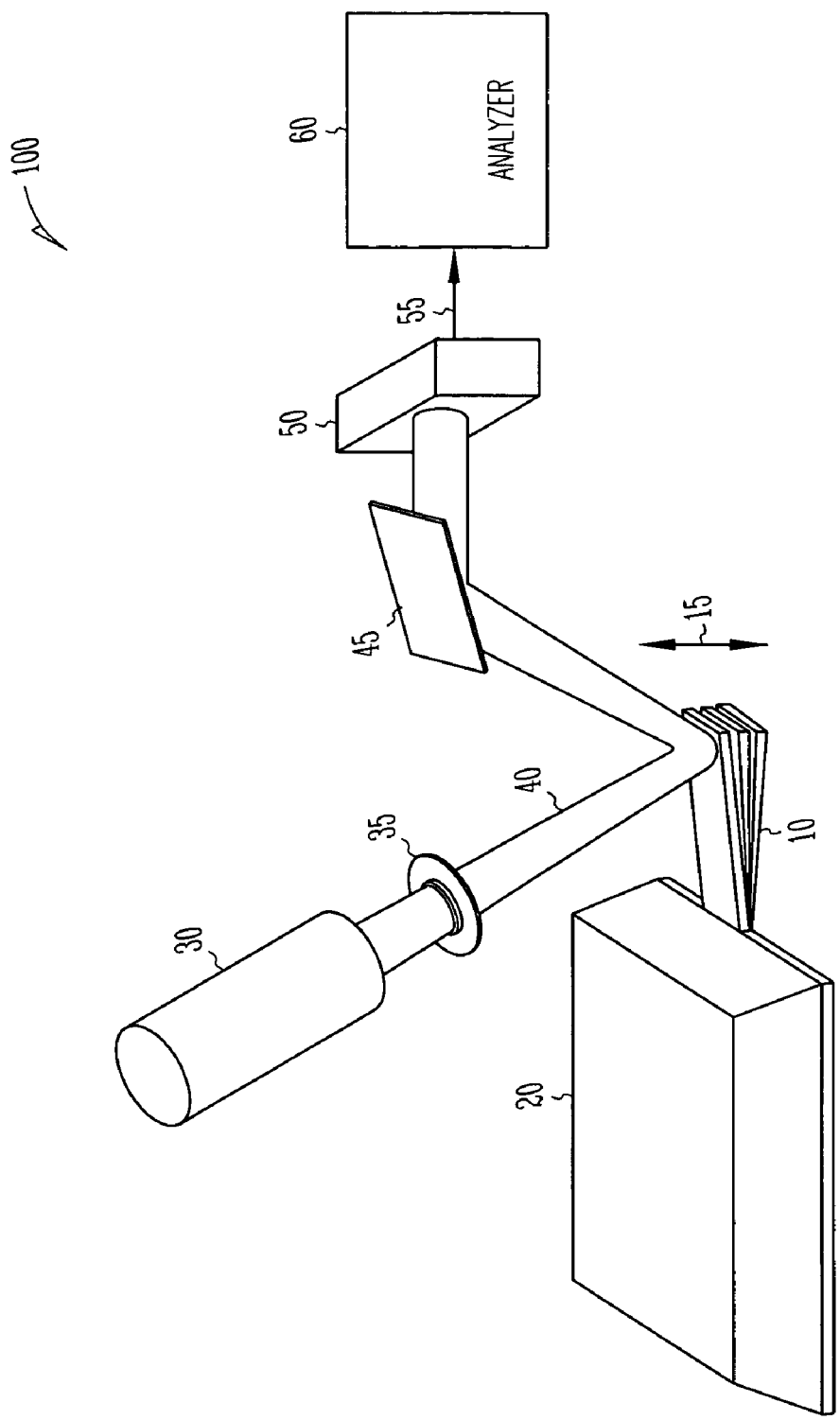
FIG. 1 illustrates one embodiment of a system according to the present subject matter.

FIG. 1 illustrates one embodiment of a system according to the present subject matter. In the figure, system 100 is suitable for the detection of E. coli or other bacterial cells. Cantilever beam 10 is affixed on one end to support 20. The other end of beam 10 is free to move in the directions indicated by arrow 15. Beam 10 vibrates at a resonant frequency when driven by ambient environmental conditions or when driven externally, by, for example, a piezo-electric device. In the embodiment shown, laser 30 projects light 40, optionally through lens 35, onto the apex of beam 10. Lens 35 focuses the light onto the apex of beam 10. Light 40 is reflected by beam 10. A mirror 45 can redirect light 40 to illuminate sensor 50. Sensor 50 generates an output signal 55 based on the vibrations of cantilever beam 10. Spectrum analyzer 60 processes output signal 55 and yields useful information.

In one embodiment, beam 10 is fabricated of silicon nitride. Preferably, beam 10 is fabricated of low stress silicon nitride. Beam 10 may also be fabricated of other materials, including for example, silicon, silicon dioxide, silicon carbide, polysilicon, carbon, diamond like carbon (DLC) film, metal, gallium arsenide or other conductor or semiconductor material. Preferably, the material used for beam 10 is conducive to photolithography processes and etching to release beam 10 from the surrounding structure. Preferably, the material used for beam 10 is conducive to fabrication of structures having the scale and geometry as herein provided. Micromachining techniques, or other suitable technology may be used to fabricate beam 10. Beam 10 may be fabricated using either bulk or surface silicon micromachining technology.

In the embodiment shown, beam 10 is substantially linear. Alternatively, beam 10 may include a helical section or multiple anchor points with various modes of freedom to enable greater sensitivity. Beam 10 can have different cross sectional shapes, including, for example, rectangular, square or round cross section.

Figure 2:
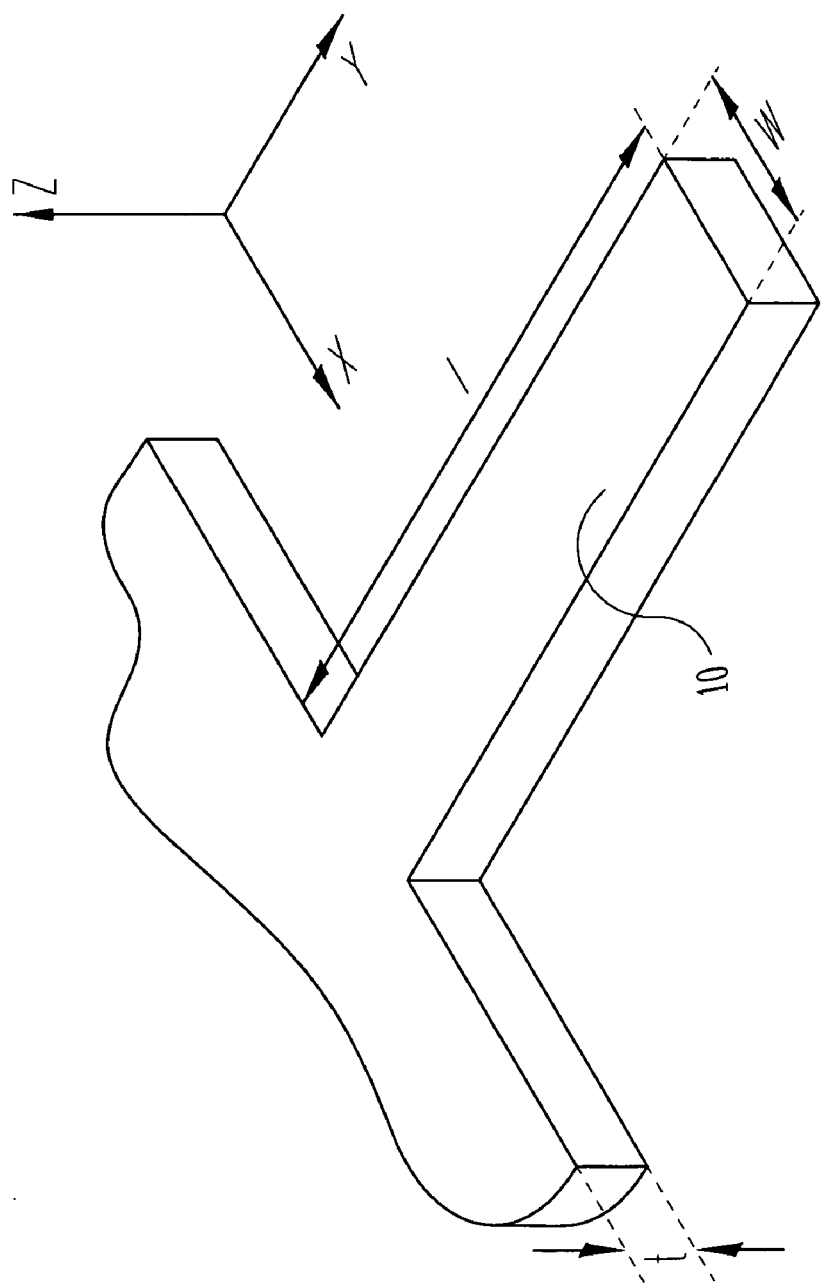
FIG. 2 illustrates representative beam geometry.

The physical dimensions of beam 10 are selected to meet desired sensitivity requirements. FIG. 2 illustrates the geometry of a typical beam 10. Preferably, beam 10 has a high aspect ratio, that is the length l, is longer than the width w, of beam 10. By way of example, but not by way of limitation, a high aspect ratio beam is one having a ratio of length to width of approximately 3.75 or more. For example, typical dimensions for the length of beam 10 can be in the range of 0.5 to 1000 μm. Typical dimensions for the width of beam 10 can be in the range of 0.1 to 50 μm. A typical dimension for the thickness t, of beam 10 can be in the range of 0.05 to 4 μm. The aforementioned dimensions are not to be construed as limitations for the present system. A coordinate system is also illustrated in FIG. 2, with the z-axis aligned with t, the x-axis aligned with w, and the y-axis aligned with l.

In the embodiment shown in FIG. 1, beam 10 vibrates in the directions of arrow 15, or substantially along the z-axis. Arrow 15 extends normal to the plane of beam 10, and thus, the vibratory mode is said to be out of plane. Other modes of vibration may also be sensed. For example, vibrations in plane may be monitored with suitable sense apparatus. Vibrations in more than one plane can also be monitored.

Support 20 is coupled to one end of beam 10. In the embodiment shown in FIG. 1, support 20 is illustrated as a rectangular housing. Support 20 can be a heavier region of the substrate upon which cantilever beam 10 is fabricated, and is thus stable relative to the vibrations of cantilever beam 10. Support 20 can be fabricated in conjunction with the fabrication of beam 10. Consequently, support 20 may also be fabricated of the same material used in the fabrication of beam 10. In addition, support 20 may be fabricated in conjunction with other integrated electronic devices, components or circuitry. The other integrated electronic devices, components or circuitry may be related or unrelated to the operation of detector system 100. For example, support 20 may be fabricated on the same substrate as digital logic gates, amplifiers, processors, memory cells, or other semiconductor devices.

Figure 3A:
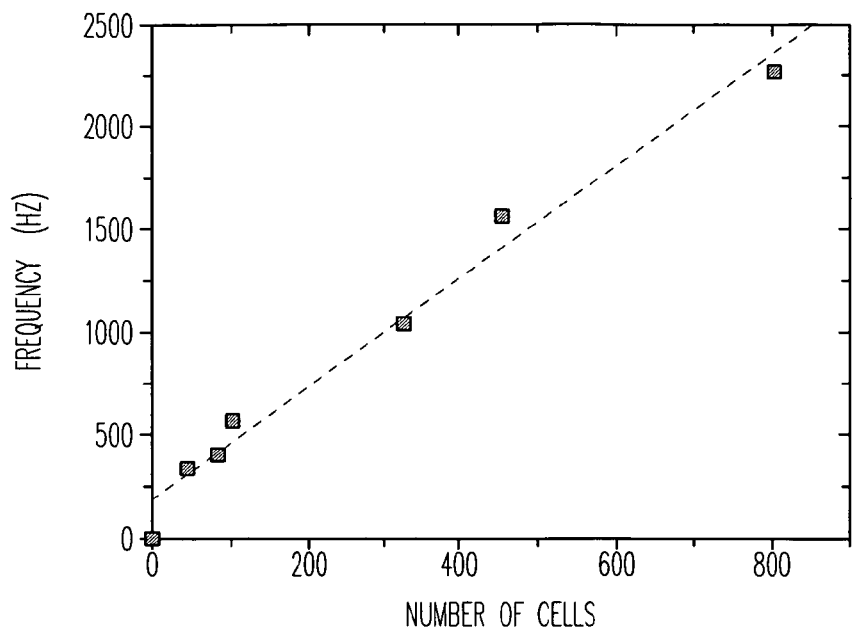
FIGS. 3A, 3B, 3C and 3D graphically illustrate a relationship between the number of cells and a frequency differential.
Figure 3B:
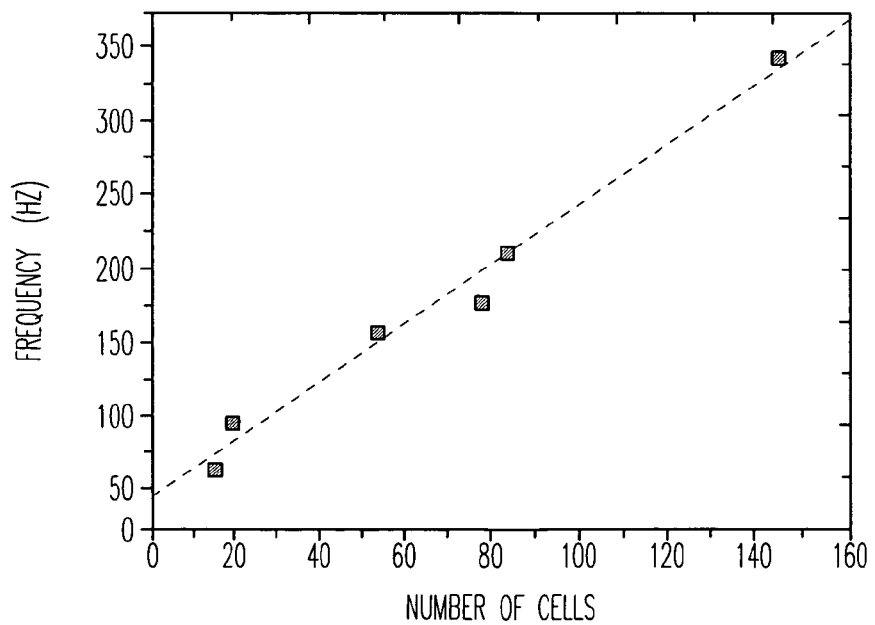
Figure 3C:
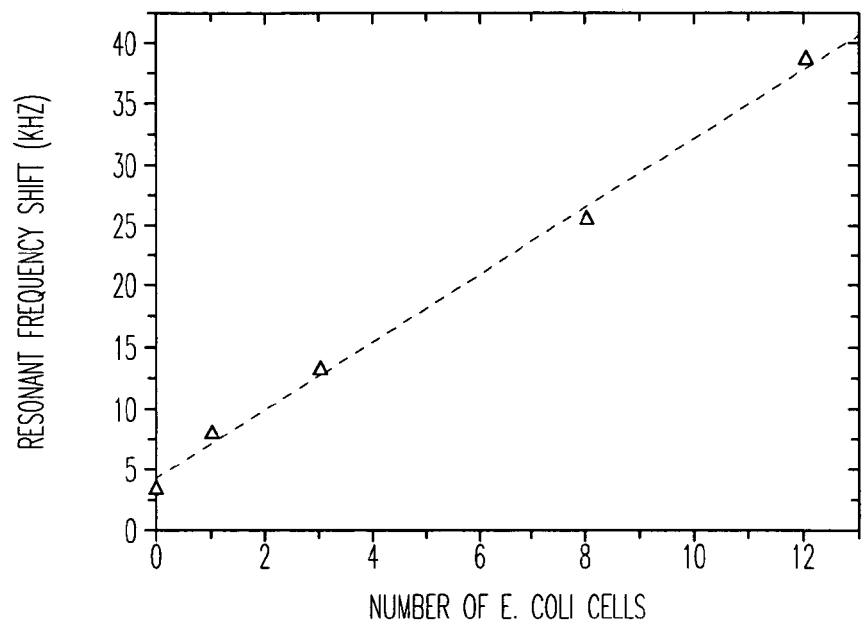
Figure 3D:
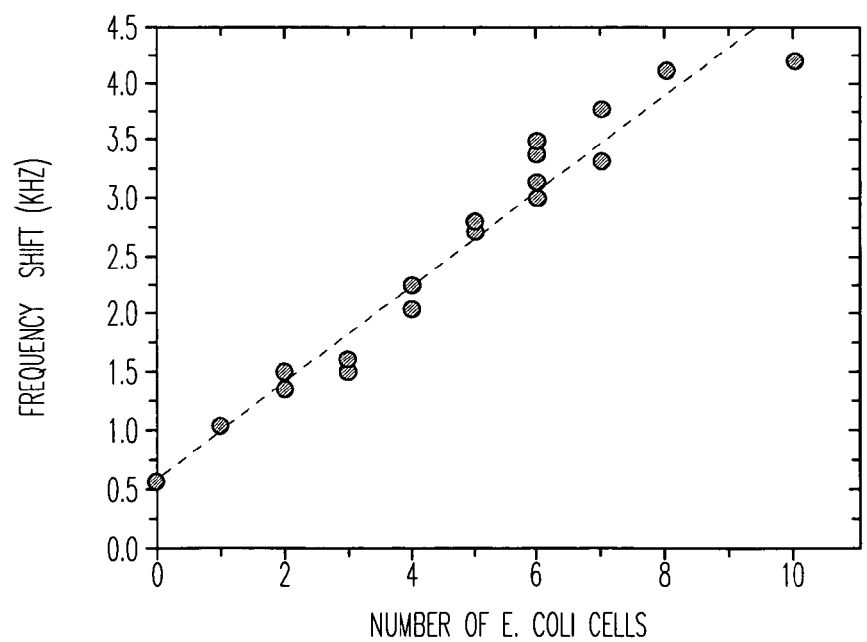

Cantilever beam 10 vibrates at a first frequency determined by the geometry, the mass, the distribution of mass, and external forces acting on beam 10. A change in the mass of beam 10 is detectable as a change in the resonant frequency of beam 10. FIGS. 3A and 3B graphically illustrate this phenomena for a particular beam sensitized for detecting E. coli cells. The number of E. coli cells is shown on the abscissa and differential frequency, measured in Hertz, on the ordinate. The number of cells is proportional to the mass change of beam 10. FIG. 3A corresponds to a cantilever beam 10 having dimensions of 100 micrometers ("μm") in length, 20 μm in width and 320 nanometers ("nm") in thickness and shows number of cells in the range of 0 to 900. FIG. 3B corresponds to a cantilever beam 10 having dimensions of 200 μm in length, 10 μm in width and 600 nm in thickness and shows number of cells in the range of 0 to 160. The graphs show the substantially linear relationship between mass and frequency differential. Deviations from linearity are explained by such factors as nonuniform loading of beam 10 as well as nonuniform flexural rigidity of beam 10 resulting from variations in the distribution of the mass of beam 10. The particular beam depicted in FIGS. 3A and 3B was effective for detecting the presence of 16 E. coli cells. FIGS. 3C and 3D illustrate measured frequency shift dependence relative to the number of bound E. coli cells for particular cantilever beams. In FIG. 3C, the beam has dimensions l=15 μm and w=5 μm. In FIG. 3D, a slightly larger beam was used having dimensions l=25 μm and w=10 μm. The figures show a linear regression fit to the data.

Beam 10, and the support structure, may be fabricated using any of a number of semiconductor fabrication techniques. An exemplary bulk micromachining fabrication process is as follows:

In one embodiment, low stress silicon nitride is applied to a substrate by low pressure chemical vapor deposition ("LPCVD") to a thickness of 320 nm. Alternatively, silicon nitride can be applied by plasma enhanced low pressure chemical vapor deposition ("PECVD") to a depth of 600 nm. Other thicknesses, as well as other deposition technologies, are also contemplated. The substrate can be a silicon wafer. Other substrates are also contemplated, including for example but not by way of limitation, gallium (such as gallium antimonide and gallium arsenide), indium (such as indium antimonide, indium arsenide and indium phosphide), and polycrystalline materials (such as polycrystalline gallium arsenide and polycrystalline indium phosphide).

The cantilever beam 10 and support 20 are defined by photolithography on a front side of the substrate wafer. The exposed silicon nitride is etched in a reactive ion etch ("RIE") chamber using carbon tetrafluoride ("$CF_4$"). The back side of the wafer is treated in a similar manner with features aligned as appropriate.

To prevent roughening of the front side silicon nitride during later processing, a layer of oxide may be deposited using PECVD to a thickness of 2 μm. The wafer is etched using potassium hydroxide ("KOH"). As back side etching of the wafer approaches the front surface, the 2 μm layer of PECVD oxide is removed by buffered (6:1) oxide etch solution. The etch is continued until the cantilever is released from the surrounding structure.

In one embodiment, the release of cantilever beam 10 is aided by using a high pressure carbon dioxide ($CO_2$) critical point dryer. The critical point dryer reduces, or prevents, morphological damage to the structure resulting from dehydration in the atmosphere due to surface tension at the liquid interface. If left unchecked, the surface tension of the solution may aggravate stiction and result in breaking of the cantilever structure. In particular embodiments, the calculated Young's Modulus of elasticity for the silicon nitride cantilever fabricated using PECVD and LPCVD is 93 gigapascal ("GPa") and 110 Gpa, respectively.

Figure 4A:
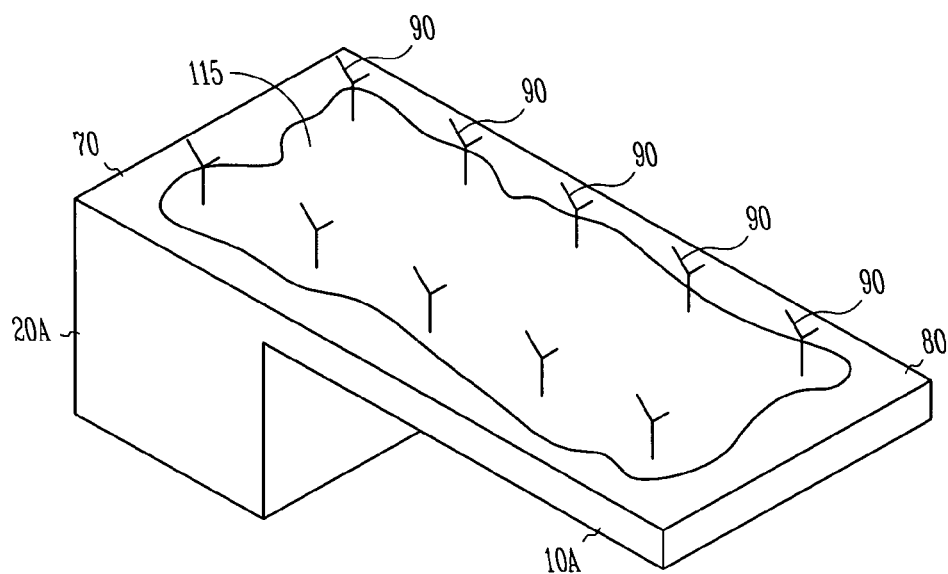
FIGS. 4A and 4B illustrate cantilever beams with bound cells on a surface.
Figure 4B:
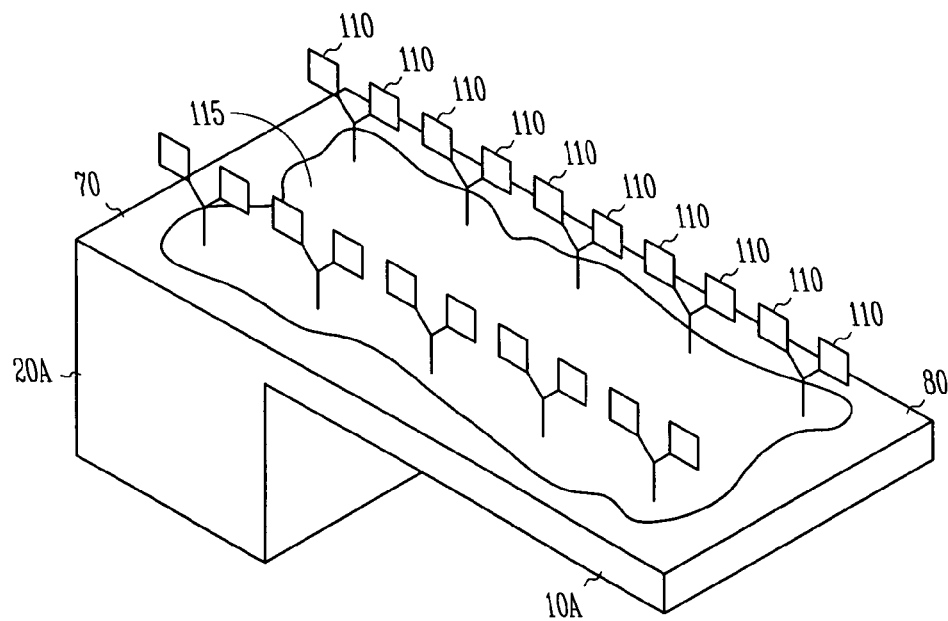

FIGS. 4A and 4B illustrate one embodiment of cantilever beam 10A having a binding partner 115 on a surface. In the figures, support 20A is represented as a base structure and is rigidly attached to further structure not appearing in the figure. Beam 10A has a first end 70 rigidly attached to support 20A and a second end 80 that is cantilevered. In one embodiment, second end 80 is free to vibrate in an out of plane mode. Binding partner 115 is immobilized on beam 10A. Binding partner 115 is conformally distributed, or coated, on all surfaces of the structure illustrated in FIG. 4A. Binding partner 115 can be localized to a particular portion of beam 10A, such as, for example, a region near second end 80. Binding partner 115 can be distributed on an upper surface of beam 10A. Binding partner 115 can be distributed on the exterior surfaces of beam 10A. Binding partner 115 can be impregnated within the interior structure of beam 10A. Binding partner 115 can be a surface coating on beam 10A and thus, selectively bind to predetermined molecules. In one embodiment, binding partner 115 includes molecules 90 that bind to complementary molecules on target cells in a "lock and key" fashion. In the embodiment of FIG. 4A, binding partner 115 includes a plurality of antibody molecules, herein represented as a plurality of "Y" shaped characters 90. FIG. 4B illustrates beam 10A having binding partner 115 at a time when complementary molecules 110 have bound with the antibody molecules 90 of binding partner 115. Binding partner 115 can bind to one or more target substances in a reversible or essentially irreversible fashion. Examples of essentially irreversible bonds may include those arising by van der Waal forces, ionic bonds, or by formation of covalent bonds. Preferably, binding does not occur by simple physical absorption of the target by beam 10 or binding partner 115 thereon.

In FIG. 4A, one embodiment of beam 10 is shown having an amount of binding partner 115 immobilized on the surface. Binding partner 115 is selected to bind to a desired target substance, or substances, wherein said bound target substance, or substances, is then detected by system 100. For example, one protein (such as an antibody) may be used as a binding partner 115 on beam 10 for purposes of detecting a second protein (such as an antigen). By way of example only, and not by way of limitation, other pairs include using a receptor for detecting a ligand such as using a cellular receptor to detect a ligand that binds to such receptor, using a protein for detecting a peptide, using a protein for detecting a DNA, using a first DNA sequence to detect a second DNA sequence, using a metallic ion to detect a chelator, and using an antibody, or an antibody fragment, for detecting an antigen or analyte. It will be recognized that the aforementioned examples bind to each other in a "lock and key" fashion by ionic bonding, covalent bonding or a combination thereof. In some cases, the binding partner may bind specifically to a single target substance or subunit thereof. Consequently, either the "lock" can be immobilized on beam 10 for detecting the "key" or the "key" can be immobilized on beam 10 for detecting the "lock." As an example, a peptide may be the binding partner on beam 10 for use in detecting a protein. The binding partner 115 immobilized on cantilever beam 10 can be DNA and thus, the present system is responsive to the substantial DNA complement. The bound, or "hybridized" DNA sequences can then be treated or "washed" under various conditions of stringency so that only DNA sequences that are highly complementary (e.g., that has high sequence identity) will be retained on beam 10.

The binding partner 115 can also bind to a plurality of substances, in which case, system 100 will indicate detection of any substance binding to cantilever beam 10. In addition, more than one binding partner 115 may be immobilized on a particular cantilever beam 10 to enable detection of multiple molecules. Multiple binding partners 115 may be immobilized in the same or different regions of cantilever beam 10.

The binding partner 115 can include an antibody for detection of an antigen, or binding partner 115 includes an antigen for detection of an antibody. Examples of antigens include proteins, oligopeptides, polypeptides, viruses and bacteria. For instance, antigens include $OMP_a$, $OMP_b$ and $OMP_c$, commonly referred to as outer membrane protein "a" "b" and "c." In such cases involving antigens, the interaction includes one or more amino acid interactions wherein the amino acids are spatially arranged to form two complementary surfaces in three dimensions. Each surface includes one or more amino acid side chains or backbones.

The binding partner 115 can include an antibody for detection of a hapten, or binding partner 115 includes a hapten for detection of an antibody. Haptens tend to be much smaller than antigens and include such compounds as transition metal chelators, multi-ring phenols, lipids and phospholipids. In such cases involving haptens, the interaction includes an intermolecular reaction of a surface of the hapten with one or more amino acids of the antibody, wherein the amino acids of the antibody are spatially arranged to form a complementary surface to that of the hapten.

The interaction between amino acids, such as antibody-antigen or antibody-hapten, arises by van der Waal forces, Lennard-Jones forces, electrostatic forces or hydrogen bonding. Consequently, immobilized binding partner 115 interacts with the targeted substance in a manner beyond that of simple absorption of analyte into a matrix of some type. The interaction of binding partner 115 with the target substance is characterized by rapid bonding, preferably bonding that is not reversible under ambient conditions, thus reducing the time required for reliable detection using system 100.

Hybrid antibodies are also contemplated for either the target substance or binding partner 115. For example, a portion of a first antibody may be cleaved and a second antibody may be bonded to the remaining portion of the first antibody, thus forming a hybridized antibody. Such an antibody may subsequently bind with two forms of antigens or haptens. As yet another example, a third antibody may be bonded to the remaining portion of the first antibody, thus enabling subsequent bonding to additional antigens or haptens. The use of hybridized antibodies in system 100 yields a detector sensitive to multiple substances and may be desirable for certain applications where detection of two or more analytes is desired.

Binding partner 115 is affixed, or immobilized, to the surface of beam 10 using any of a number of techniques, including absorption, covalent bonding with or without linker or spacer molecules or complexation. For example, in one embodiment, a cantilever beam 10 is prepared for detection of *E. coli* cells using the following method:

After releasing cantilever beam 10 from the surrounding structure, antibodies to *E. coli* were prepared and immobilized to beam 10. The *E. coli* cells were affinity purified (by means of affinity chromatography) and isolated from a serum pool from goats immunized with whole cells of *E. coli* serotype O157:H7 (Kirkegaard & Perry Laboratories Inc., Gaithersburg, Md.). A phosphate buffer saline (0.1M $NaH_2PO_4$, 0.2M $Na_2HPO_4$), (hereinafter "PBS"), was prepared from 1.38 g $NaH_2PO_4H_2O$ and 2.84 g $Na_2HPO_4$, diluted to 100 ml with deionized water. *E. coli* antibody concentration of 1 mg/ml was prepared by adding 1 ml of 0.3M Sodium Phosphate Buffer (pH 7.4) to 1 mg vial of antibodies. The vial was rotated until total dissolution was achieved and the solution was then incubated at 37° C. for 30 minutes. The anti-*E. coli* antibodies may be immobilized on the surface of beam 10 to an average thickness of 40 nm. Thicknesses greater than or less than 40 nm are also contemplated.

The *E. coli* O157:H7 cells were cultured in Luria broth (a nutrient broth used to support the growth of *E. coli*) and enumerated (colony forming units ("CFU") per mL) on Luria agar. Cells were heat-inactivated by immersing 1 mL aliquots of cell culture (in 1.5 mL Eppendorf tubes) in boiling water for approximately 90 seconds. Inactivation of the cells was confirmed by spread plating 100 μL of the heat-treated cell culture onto Luria agar and plates were read after an incubation period of 24 hours at 37° C. Heat-treated cells were then pelleted by centrifugation (2040×g for approximately 10 minutes), and re-suspended in PBS. Serial 10-fold dilutions of the re-suspended cells were performed in PBS from $10^9$ to 106 CFU/mL.

Figure 5A:
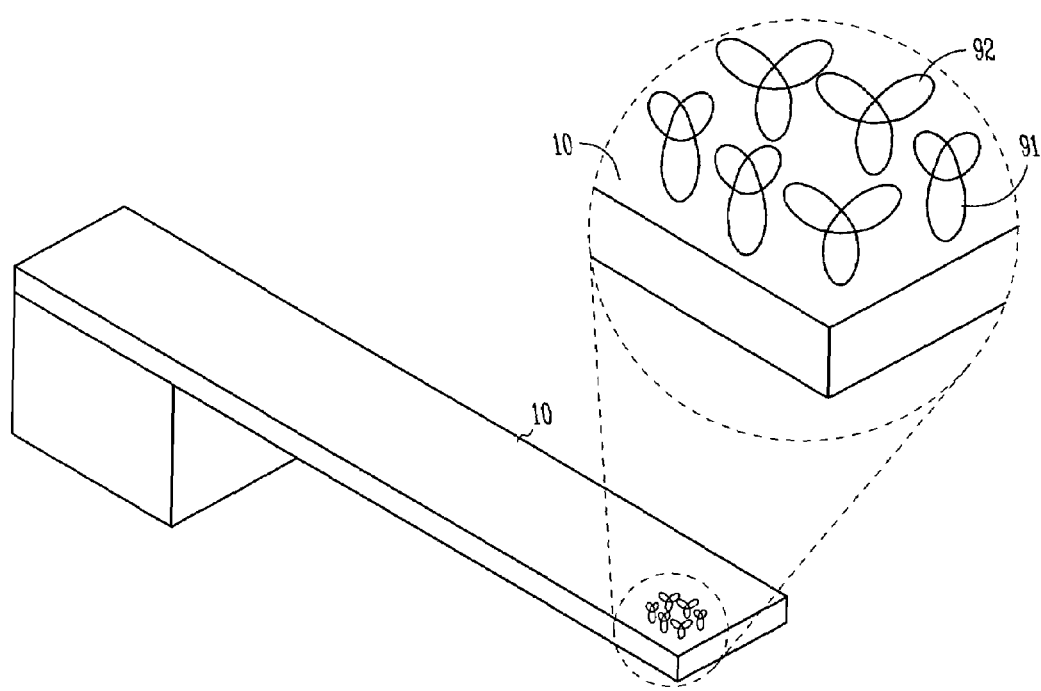
FIGS. 5A and 5B illustrate a cantilever beam having a binding partner on a surface.
Figure 5B:
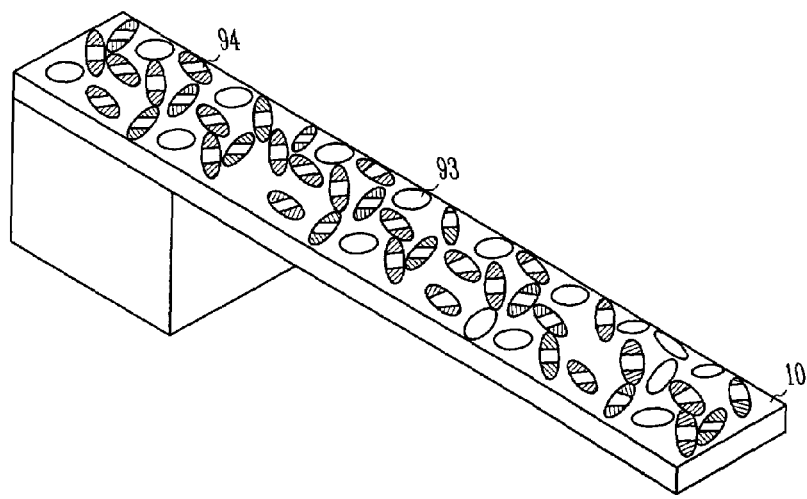
Figure 6A:
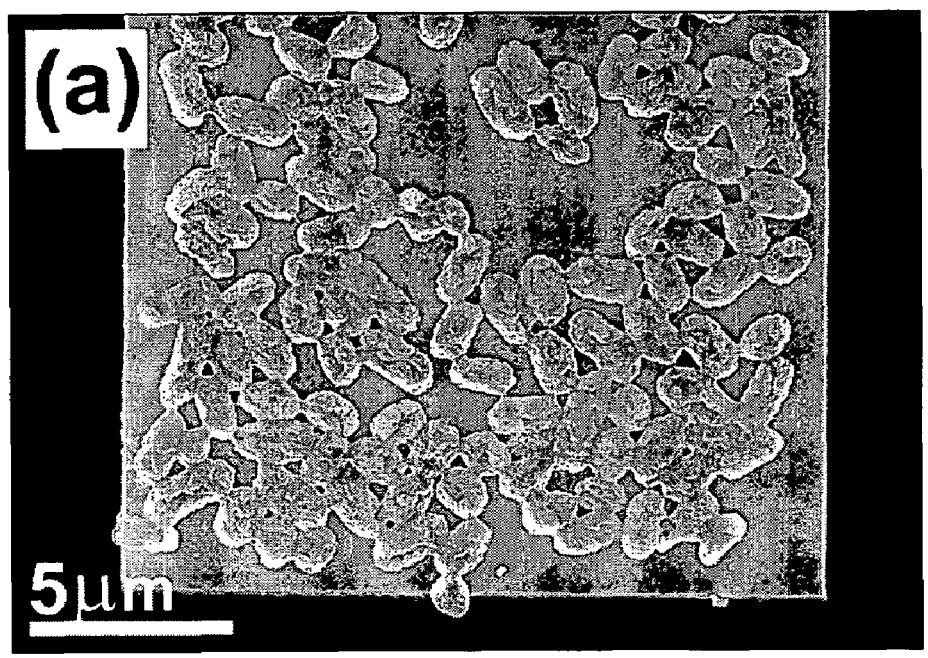
FIGS. 6A, 6B, 6C and 6D illustrate scanning electron micrographs showing a random distribution of bound cells immobilized on the surface of four different cantilever beams.
Figure 6B:
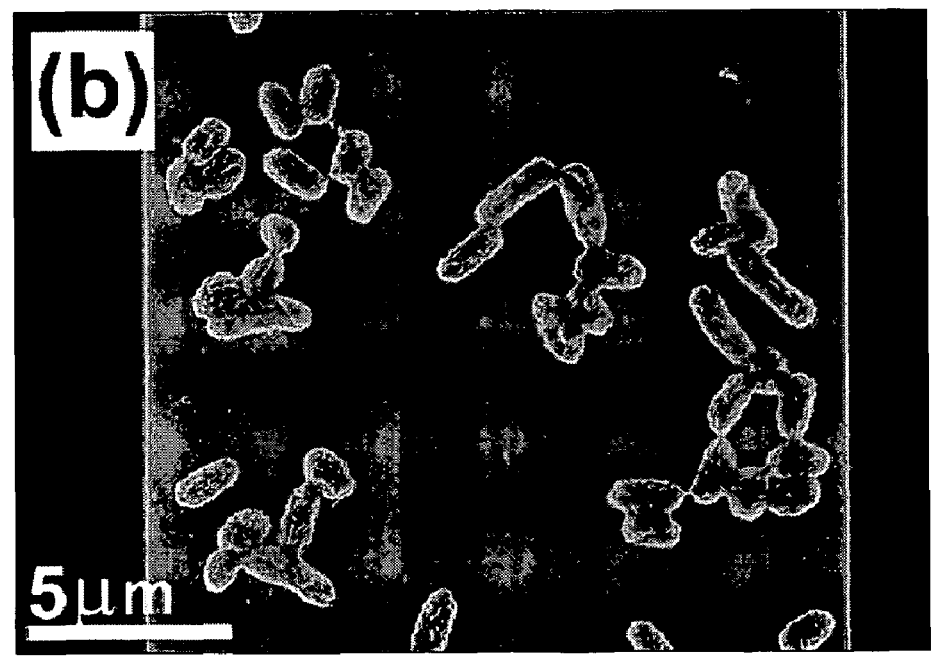
Figure 6C:
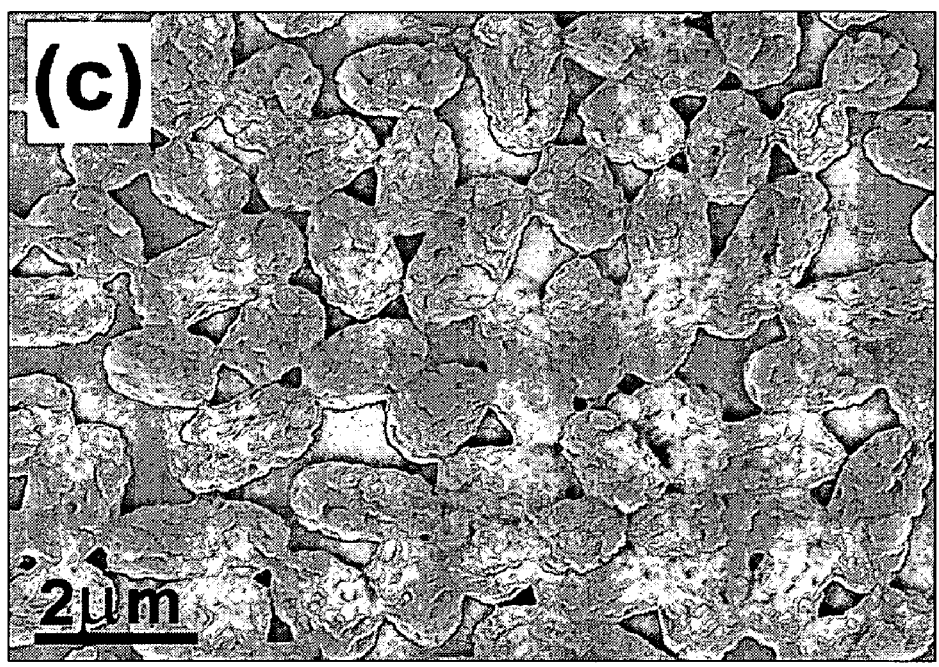
Figure 6D:
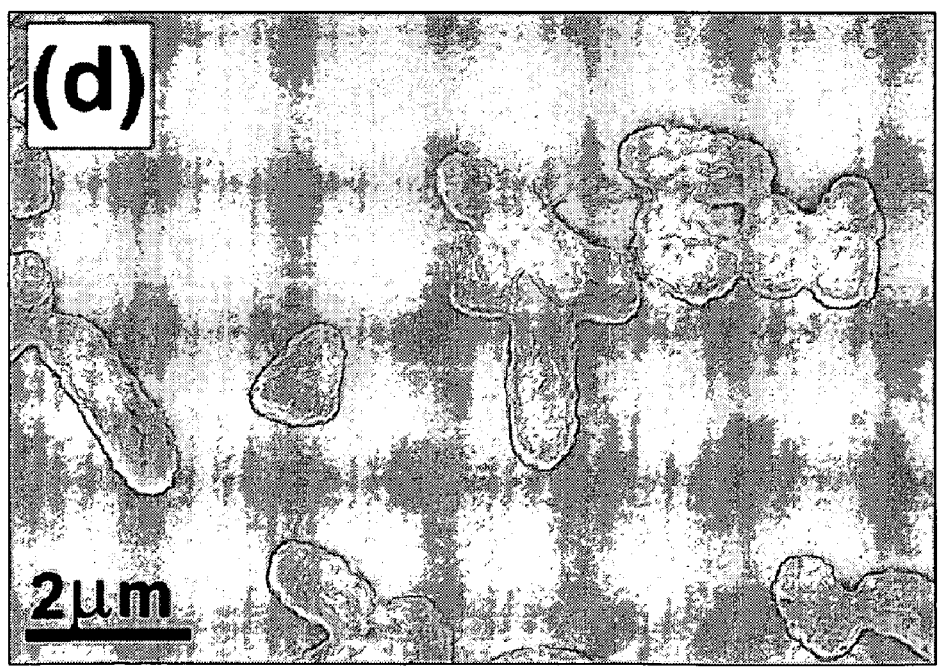
Figure 7:
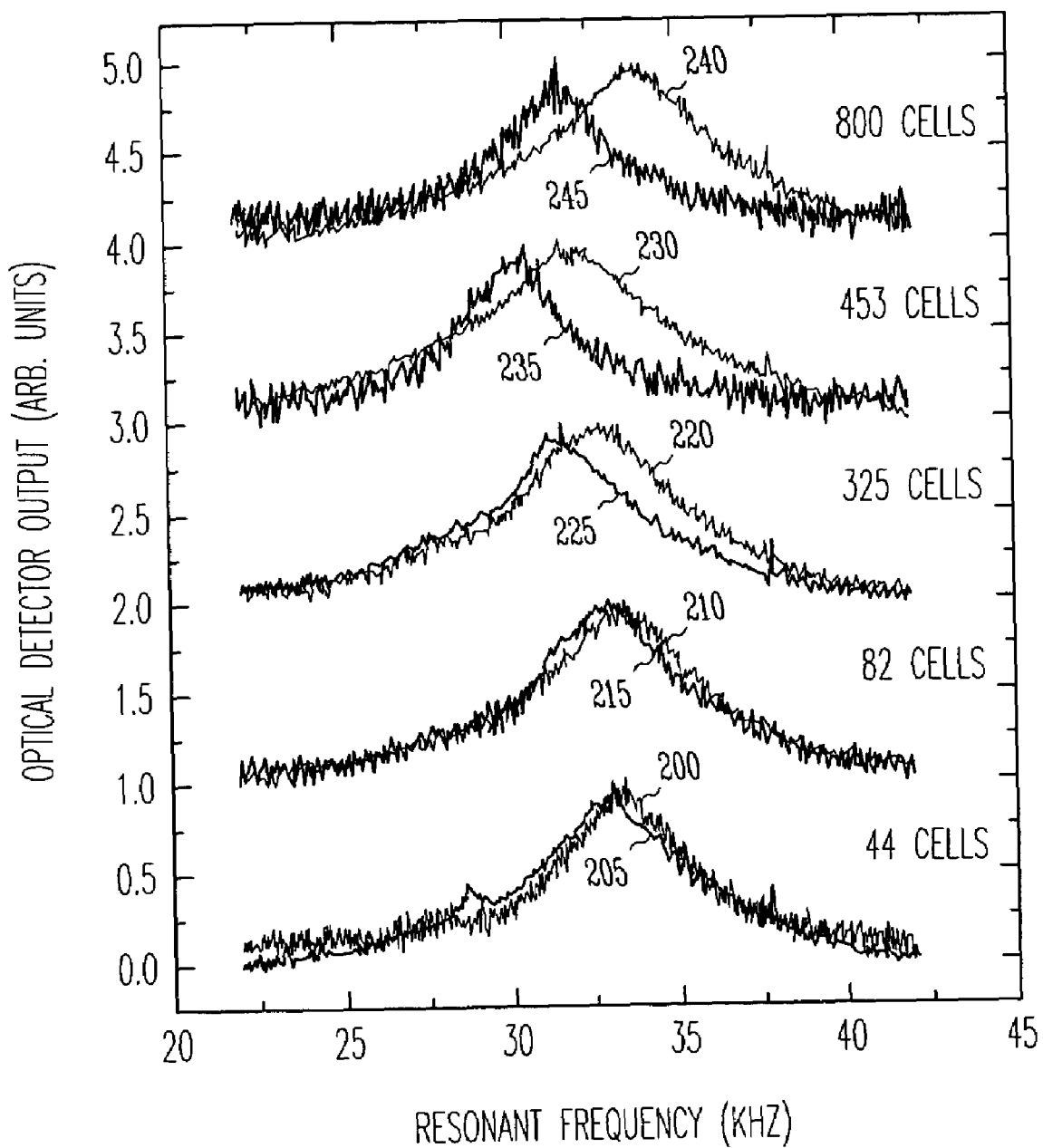
FIG. 7 graphically illustrates resonant frequency as a function of detector output.
Figure 8:
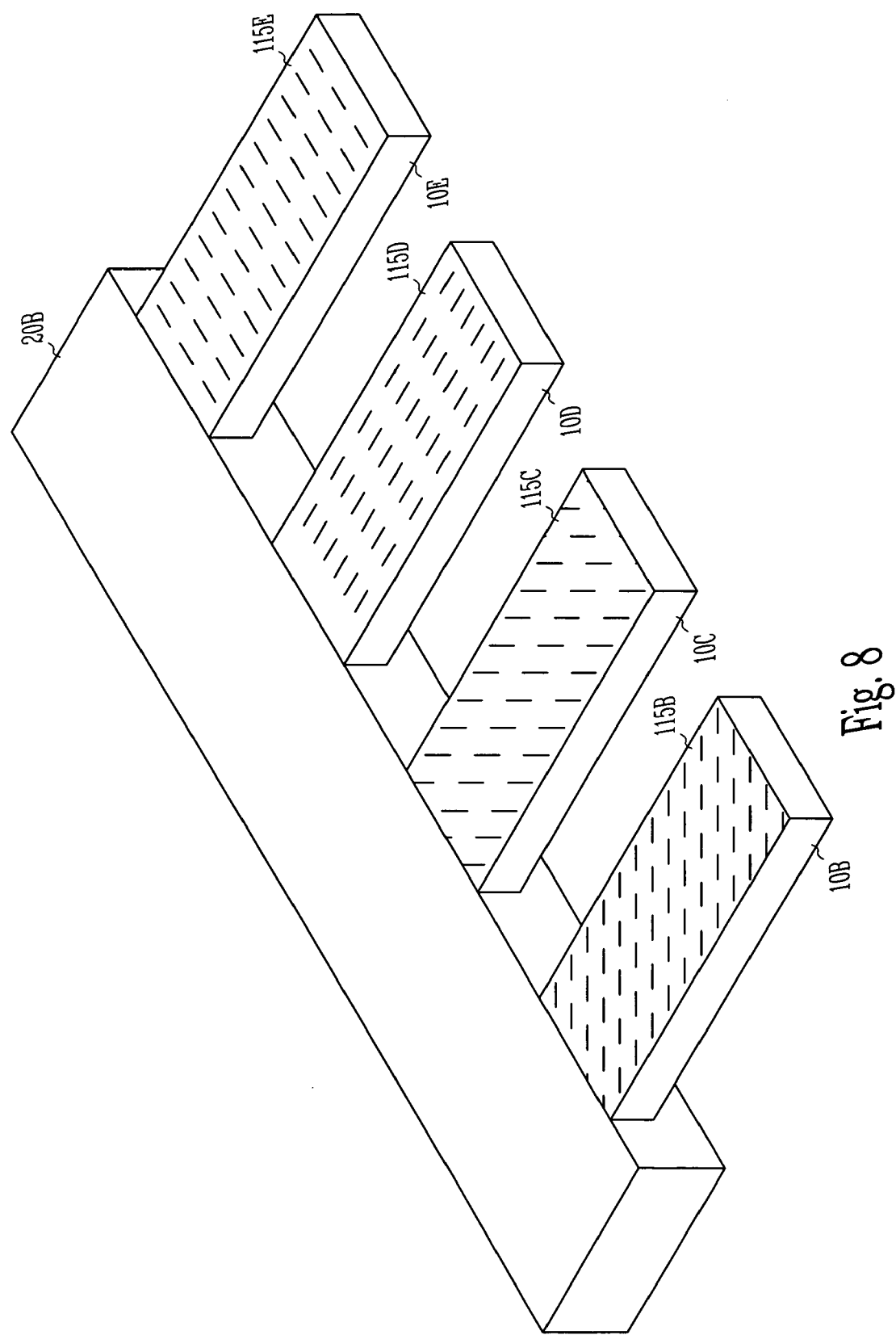
FIG. 8 illustrates an array of cantilever beams.

After releasing beam 10 from the surrounding structure, the resonators were immersed in a solution of *E. coli* serotype O157:H7 antibodies for 5 minutes, rinsed in deionized water, and then blown dry with nitrogen. FIG. 5A schematically illustrates the resulting beam 10. In FIG. 5A, element 91 represents the upper surface of beam 10 and element 92 represents antibodies bound to beam 10. Following antibody coating, the cantilevers were immersed into a solution of PBS with suspended *E. coli* cells ranging in concentration from $10^6$–$10^9$ *E. coli* cells/ml for approximately 15 minutes. The cantilevers were subsequently rinsed in a 0.05% solution of Tween® (ICI Americas, Inc.), rinsed in water, and then blown dry with nitrogen. FIG. 5B represents the resulting beam 10. FIG. 5B represents a scanning electron micrograph showing a random distribution of bound *E. coli* cells immobilized on the surfaces of several cantilevers. In FIG. 5B, elements 93 and 94 represent bound *E. coli* cells.

FIGS. 6A, 6B, 6C and 6D illustrate scanning electron micrographs showing a random distribution of bound cells immobilized on the surface of four different cantilever beams. To reduce charging effects during scanning electron microscope ("SEM") imaging, the samples were prepared by evaporating a thin (under 10 nm) layer of Au/Pd. FIGS. 6A, 6B, 6C and 6D were prepared in a similar manner, using $10^8$ *E. coli* cells per ml, and show a random distribution of the cells.

Other methods for immobilizing binding partner 115 to beam 10 are also contemplated. For example, binding partner 115 can be covalently bonded to a surface of beam 10. Binding partner 115 can also be non-covalently bonded to a surface of beam 10. Binding partner 115 can be bonded by absorption to a surface of beam 10. In particular, amino chemistry, carboxyl chemistry, and carbohydrate chemistry techniques may be used to bond binding partner 115 to a surface of beam 10.

Exposure of cantilever beam 10 to the test solution may be achieved by any suitable means. Continuing with the example of the detection of *E. coli*, one representative method includes immersing cantilever beam 10 in a buffered aqueous medium containing different concentrations of *E. coli* cells ranging from $10^6$ to $10^9$ *E. coli* cells/ml. The beam may be incubated in the medium at room temperature for a period of time and then rinsed, to remove unbound components of the medium, and dried in a nitrogen atmosphere. The incubation period can be approximately fifteen minutes. Rinsing may be in a solution of Tween® (ICI Americas, Inc.) to remove any loosely bound cells. Rinsing may also be in deionized water. The *E. coli* cells are not dissolved in the water.

In the embodiment shown, cantilever beam 10 resonates under ambient conditions. The geometry and dimensions of beam 10 enable measurable differences in resonant frequency without the use of external oscillatory driving forces. Ambient conditions include any thermal mechanical noise. Ambient conditions include airborne vibrations. System 100 can operate in a vacuum, thus reducing the influence of airborne vibrations.

Alternatively, however, cantilever beam 10 can resonate under external forces. External driving of cantilever beam 10 yields a greater amplitude of oscillation. In one embodiment, the driving frequency is swept through a range of frequencies and oscillation amplitude of cantilever beam 10 is measured. An example of external force includes the forces exerted by a piezoelectric driver. Magnetic drivers are also contemplated wherein a changing magnetic field drives beam 10. Other field forces may also be used to drive beam 10. For example, the support structure for cantilever beam 10 can be externally driven at a particular frequency.

With reference to FIG. 1, analyzer 60 derives information from sensor 50. Sensor 50 can include a split photodiode or two separate photodetectors and analyzer 60 can comprise a spectrum analyzer. A common spectrum analyzer presents signal amplitude information as a function of frequency. In one embodiment, the light reflected from cantilever beam 10 falls first, on one portion of photodiode 50, and second, on another portion of photodiode 50. This alternating illumination of photodiode 50 generates an alternating output signal. Analyzer 60 receives the alternating output signal and displays information corresponding to the resonant frequency of cantilever beam 10.

FIG. 7 is a compilation of five representative displays appearing on the screen of analyzer 60. The abscissa marks the resonant frequency, in kilohertz, ("kHz") and the ordinate marks the output of sensor 50, herein labeled as Optical Detector Output and calibrated in arbitrary units. In one embodiment, the output of sensor 50 is a varying voltage, and thus, the ordinate corresponds to output voltage. The output of sensor 50 can be a varying resistance, in which case, the ordinate may correspond to resistance. The lower pair of curves, marked 200 and 205 in FIG. 7, corresponds to a resonating beam 10 having detected 44 cells of *E. coli* bacteria in a test solution. Curve 200 illustrates detector output as a function of frequency for beam 10 at a time after affixation of immobilized binding partner 115 as herein described and prior to exposure to the test solution. Curve 205 illustrates the same beam 10 after exposure to the test solution. Resonance occurs at the frequency corresponding to the peak output. The difference between the resonant frequency of curve 200 and that of curve 205 is a function of the mass difference. In the case of curves 200 and 205, that difference in mass represents the binding of 44 cells of *E. coli* bacteria to beam 10.

Curves 210 and 215 illustrate a typical resonant frequency differential using a similar cantilever beam 10 according to the present subject matter when detecting the presence of 82 cells of *E. coli* bacteria in a test solution. Curves 220 and 225, curves 230 and 235, and curves 240 and 245 illustrate typical results with test media having 325, 453 and 800 cells of *E. coli* bacteria, respectively.

FIG. 8 illustrates one embodiment of the present subject matter having an array of four cantilever beams, marked herein as 10B, 10C, 10D and 10E. In the figure, each of the four beams 10B, 10C, 10D and 10E are arranged in a linear manner and coupled rigidly to common support 20B. Each beam is shown having an immobilized binding partner 115B, 115C, 115D and 115E on a surface of a beam. More or less cantilever beams assembled on a common support are also contemplated.

In the embodiment shown in the figure, each of the plurality of cantilever beams is arranged along one edge of a linear support. Other configurations are also contemplated. For example, each of the plurality of beams can be arranged on two or more edges of a geometrically shaped support or each of the plurality of beams can be arranged in a circular or oval configuration. One dimensional and two dimensional configurations for the arrangement of cantilever beams are contemplated.

Referring again to an array of cantilever beams, of which FIG. 8 depicts one example, each of the binding partners 115B, 115C, 115D and 115E may be distinct from each other. In the figure, the dashed lines on the upper surface of the cantilever beams are aligned on different axis and may be interpreted as denoting different binding partners. In this manner, the cantilever beam system of FIG. 8 may be used to determine if a test sample includes any element that bind with binding partners 115B, 115C, 115D or 115E.

Any suitable technique may be used to immobilize a particular binding partner 115 to a particular cantilever beam 10 within an array of cantilever beams. In one embodiment, a photoactivation technique is used to immobilize a particular binding partner 115 to a particular cantilever beam 10. For example, light activation of a particular cantilever beam 10 can activate a photosensitive chemical coating and enable subsequent bonding of the particular binding partner 115 to the activated cantilever beam 10. A laser light source can be used to activate a particular cantilever beam 10. Light of a particular wavelength can also be used to activate, and affix, a binding partner 115 to a particular cantilever beam 10. Cantilever beam 10 may be a single beam or it may be a single beam in an array of other cantilever beams 10.

In one embodiment, a desired binding partner 115 is applied to a particular cantilever beam 10 in an array using a manifold. The manifold can include a series of capillaries having a first end aligned to transfer a fluid to each of a plurality of cantilever beams and a second end that enables introduction of the fluid on a macro level. In similar fashion, a tubule may be used to immobilize a particular binding partner on a single cantilever beam 10 or to a single cantilever beam 10 in an array of other cantilever beams 10.

In an array configuration, at least two cantilever beams can be prepared with the same immobilized binding partner 115. If a plurality of cantilever beams within an array are prepared with each beam 10 coated with the same binding partner 115, then the system offers broad area coverage for detecting a particular cell. In addition, using a common binding partner 115 on multiple cantilever beams 10 provides redundancy.

In an array configuration, each beam 10 in the plurality of beams in an array can have a different geometry. In particular, a first beam 10 may have a high aspect ratio and a second beam 10 may have a low aspect ratio. In such a case, each beam 10 has a different resonant frequency. In an array having beams of different geometry, the binding partner 115 coating on each beam 10 may be the same or it may be different.

Detecting the frequency response of cantilever beam 10 may be achieved by any suitable means. An optical sensor can be used to detect the frequency response. One embodiment of an optical sensor includes laser light reflected by a portion of the cantilever beam 10 wherein the reflected light is detected by a photodiode. The laser light may emanate from a laser diode. Preferably the light is substantially monochromatic and collimated. In an embodiment having a plurality of cantilever beams, a single laser light source illuminates multiple cantilever beams. Alternatively, in an array having a plurality of cantilever beams, a single photodiode, or other sensor, monitors the frequency response of multiple cantilever beams. Each cantilever beam 10 in an array may be monitored individually by a single laser light and a single sensor. Each cantilever beam 10 in an array can be aligned to reflect light to a particular one of a plurality of photodiodes. The photodiode can include a plurality of photodiodes arranged in a manner to provide output signals that corresponds to the frequency response of a cantilever beam 10. The frequency response of a particular cantilever beam 10 within a plurality of cantilever beams may be discerned using electronic means.

Other means of deriving, or analyzing, the frequency response of a cantilever beam 10 are also contemplated. In one embodiment, movement of the cantilever beam 10 is detected based on a change in capacitance. For example, cantilever beam 10 serves as one electrode of a capacitor and a second electrode is held in a fixed position near the cantilever beam. Capacitance between the first and second electrode will vary as a function of the movement of cantilever beam 10. As another example, movement of cantilever beam 10 may be used to change the thickness, or amount, of dielectric material between beam 10 and a stationary electrode. Changes in dielectric thickness, or amount, are measurable as a frequency response. In one embodiment, piezoelectric or piezoresistive methods are used to detect the movement of cantilever beam 10. Piezoelectric detection involves generating an electric signal when the material is subjected to stress and piezoresistive detection involves sensing changes in resistance based on a stress in cantilever beam 10. Magnetic detection involves conductor movement relative to a magnetic field. Current in the conductor may be sensed. Cantilever beam 10 can serve as the moving conductor in a stationary magnetic field.

The output of the sensor can be digitized and communicated to a processor. The processor executes programming to discern the differential frequency, and thus the mass difference.

Each of the aforementioned methods of detecting the frequency response may be used in an embodiment of the present system. For example, multiple optical sensors may be used for an array of a plurality of cantilever beams. Alternatively, a single optical sensor may be used to monitor an array of a plurality of cantilever beams.

In one embodiment, an array of cantilever beams is fabricated wherein some beams are tailored to detect a first type of cell and a second set of beams are tailored to detect a second type of cell. For example, the aspect ratio of a cantilever beam may be selected to respond with greater sensitivity to a cell having a particular mass. Geometric dimensions, the method of fabrication, and the material selected for the cantilever beam are some of the parameters that may be tailored to achieve a desired sensitivity.

In addition, the environment in which beam 10 operates has an effect on the sensitivity of the present subject matter. In the viscous regime, for example, the atmospheric pressure operating on beam 10 will produce a dampening effect due to the viscosity of the air. Increased dampening effects will degrade the sensitivity of the detector. The quality factor Q of cantilever beam 10 is proportional to the inverse square root of the atmospheric pressure. In one embodiment, a beam operating in an environment of atmospheric pressure of 1 atm (approximately 760 mm Hg) and at room temperature (approximately 25° C.), may have a quality factor Q of between 5 and 8. With a Q in this range, a particular beam 10 can detect approximately 44 bound cells of bacteria, such as E. coli bacteria. Sensitivity increases with increased quality factor Q. Increased sensitivity of the present subject matter can enable detection of both single E. coli bacteria and single monoatomic layers.

In the molecular regime, on the other hand, the quality factor is inversely proportional to the pressure. Therefore, when operated in a vacuum of 1 mTorr at room temperature, the quality factor Q is on the order of $10^4$ for one embodiment. When operated in such a vacuum, the present subject matter can detect a mass in the range of $14.8 \times 10^{-15}$ grams, and when operated in a standard atmosphere, can detect a mass 100 times larger. In addition, the mass distribution on the length of beam 10 will affect sensitivity.

The resolution of the frequency spectra is related to the width of the peak, and thus, the quality factor Q. Resolution can be 0.1 Hz when operating in a vacuum and 10 Hz in standard atmosphere.

The sensitivity of an embodiment of the present system is a function of the slope of the relationship as illustrated in FIGS. 3A, 3B, 3C and 3D. In FIGS. 3A and 3B, the sensitivity is approximately 6.81 and 5.115 Hz/pg, respectively. FIGS. 3C and 3D show sensitivities of approximately 7.08 Hz/fg and 1.04 Hz/fg for a beam having l=15 µm, w=5 µm and l=25 µm, w=10 µm, respectively (l is the length and w is the width of the beam). Sensitivities greater than 7.08 Hz/fg or less than 6.81 Hz/pg can also be achieved.

Further increases in sensitivity are also possible. For example a single E. coli bacteria cell as well as a single monoatomic layer can be detected, as explained herein. A monoatomic layer of hexamethyldisiloxane (HMDS), having a mass of $14.8 \times 10^{-15}$ g (that is, 14.8 femtograms), was measured using a surface micromachined cantilever beam fabricated using e-beam lithography and operated in a vacuum using an interferometric laser configuration.

Figure 9:
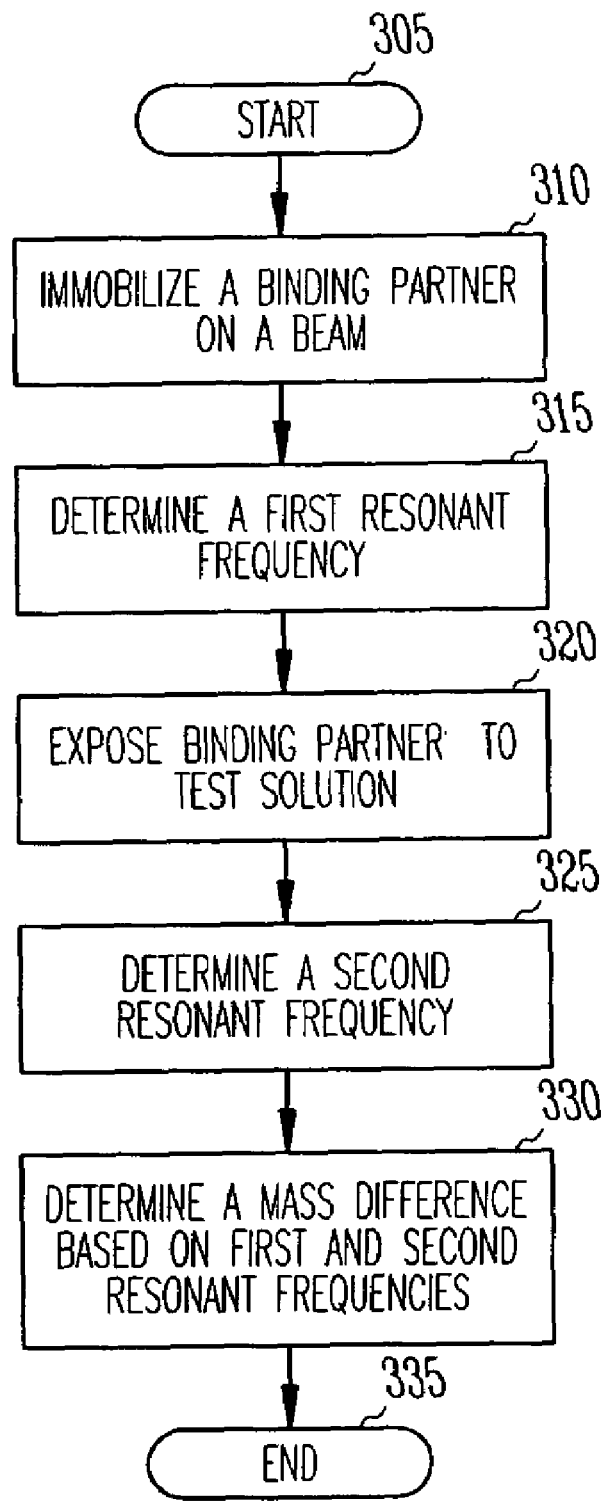
FIG. 9 illustrates a flow chart of a method pursuant to the present subject matter.

FIG. 9 illustrates a flow chart of a method pursuant to the present system. Beginning at 305, it is assumed that cantilever beam 10 has been fabricated and suitable differential frequency response detection resources are aligned. At 310, a binding partner 115 is immobilized onto cantilever beam 10. The immobilized binding partner 115 couples to the complementary molecule and securely holds the complementary molecule with respect to cantilever beam 10. At 315, a first resonant frequency is determined for cantilever beam 10 along with binding partner 115. At 320, binding partner 115 on cantilever beam 10 is exposed to the test sample suspected of containing the complementary molecule. In one embodiment, this entails immersing the cantilever beam 10 in the test sample which can be a solution, dispersion, or suspension in an organic or inorganic liquid such as water. At 325, a second resonant frequency is determined for cantilever beam 10, binding partner 115, and any complementary molecules that have been immobilized by binding partner 115. At 330, the method continues by determining a mass difference based on the first and second resonant frequencies. Determining a mass difference may be accomplished using a look up table or by executing programming on a suitable processor. The method ends at 335.

As previously noted, beam 10 may be fabricated by methods other than bulk micromachining. For example, beam 10 may also be fabricated using surface micromachining techniques.

By way of comparison, bulk micromachining entails removal of a substrate by etching whereas surface micromachining entails a sequence of depositions followed by selective removal of material. The material removed is defined by lithographic techniques. Bulk micromachining techniques are complicated by backside alignment concerns as well as thickness variations across the surface of the wafer. Surface micromachining may ameliorate such issues and enable fabrication of more complex structures having smaller dimensions. Surface micromachining may also yield a more sensitive resonator.

The frequency response of a surface micromachined device may be measured using interferometric means. By way of overview, interferometric measurement entails laser light directed at surface of beam 10. A first portion of the incident light is reflected by the surface of beam 10 and a second portion of the light passes through the beam and is reflected by the underlying substrate. Vibrations of beam 10 produce an interference pattern of varying light intensity in the total reflected beam. A single photodetector cell can transduce the variations in the intensity of the reflected light. The output signal from the photodetector can be displayed on a spectrum analyzer.

Figure 10:
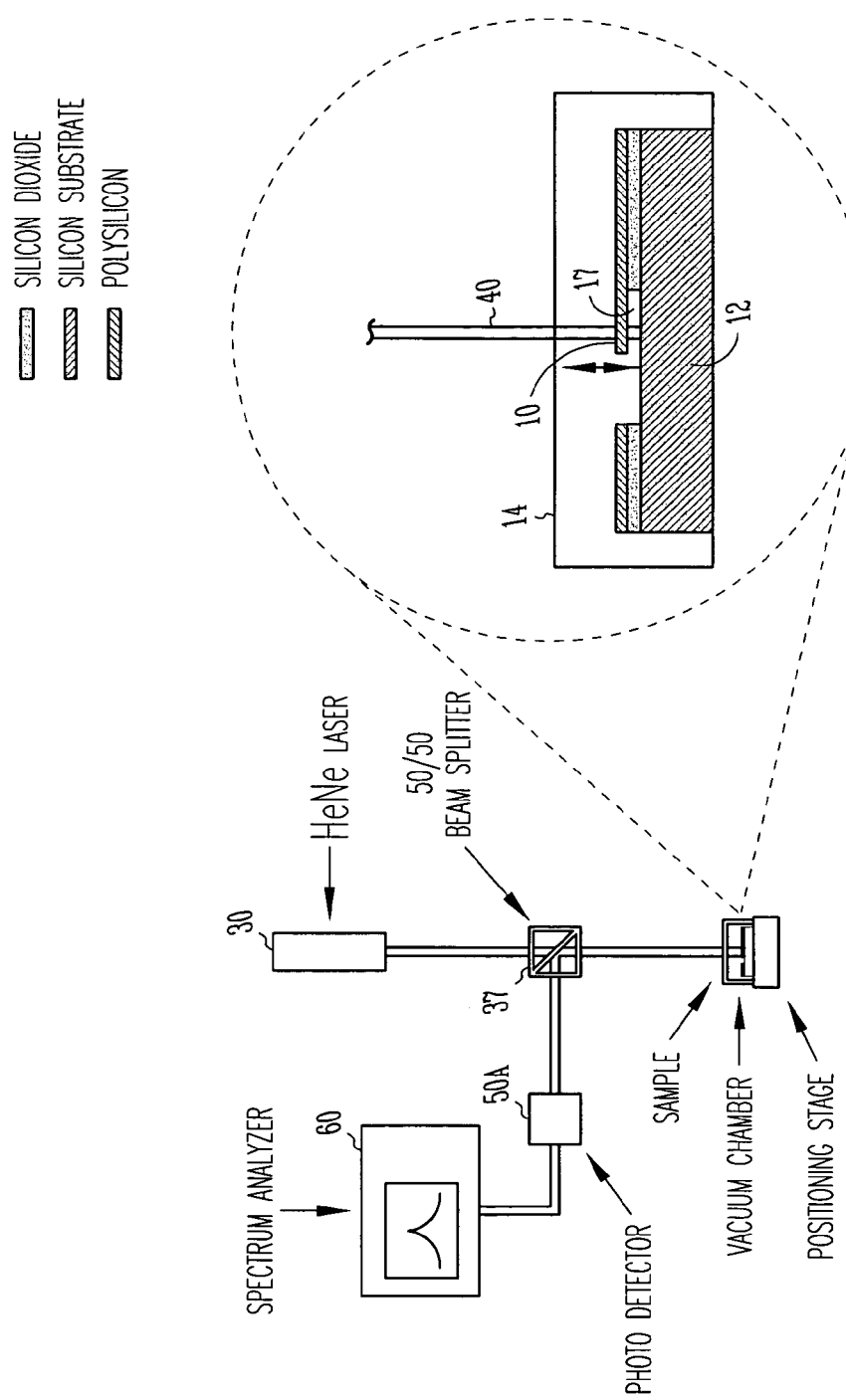
FIG. 10 illustrates schematically a configuration for measuring the frequency response of a beam.

One configuration for test apparatus is illustrated in FIG. 10. FIG. 10 also includes a magnified view of a portion of the test apparatus. In the figure, laser 30 projects incident light 40, through beam splitter 37, to beam 10. Light reflecting from the top surface of beam 10 is transmitted to beam splitter 37 and further reflected onto photodetector 50a. In addition, a portion of the incident light falling on the resonator passes through beam 10, passes through air gap 17 beneath beam 10 and is reflected by substrate 12 located under beam 10. Light reflected by substrate 12 again passes through beam 10 and is reflected by beam splitter 37 and is incident on photodetector 50a. As the beam 10 resonates, the intensity of the reflected beam is modulated by the interference of the light ray, or beam, reflecting off the surface of vibrating beam 10 and the light beam reflected off the underlying substrate. The interference patterns thus generated can be detected by photodetector 50a and an output signal from the photodetector is then applied to spectrum analyzer 60.

Figure 12:
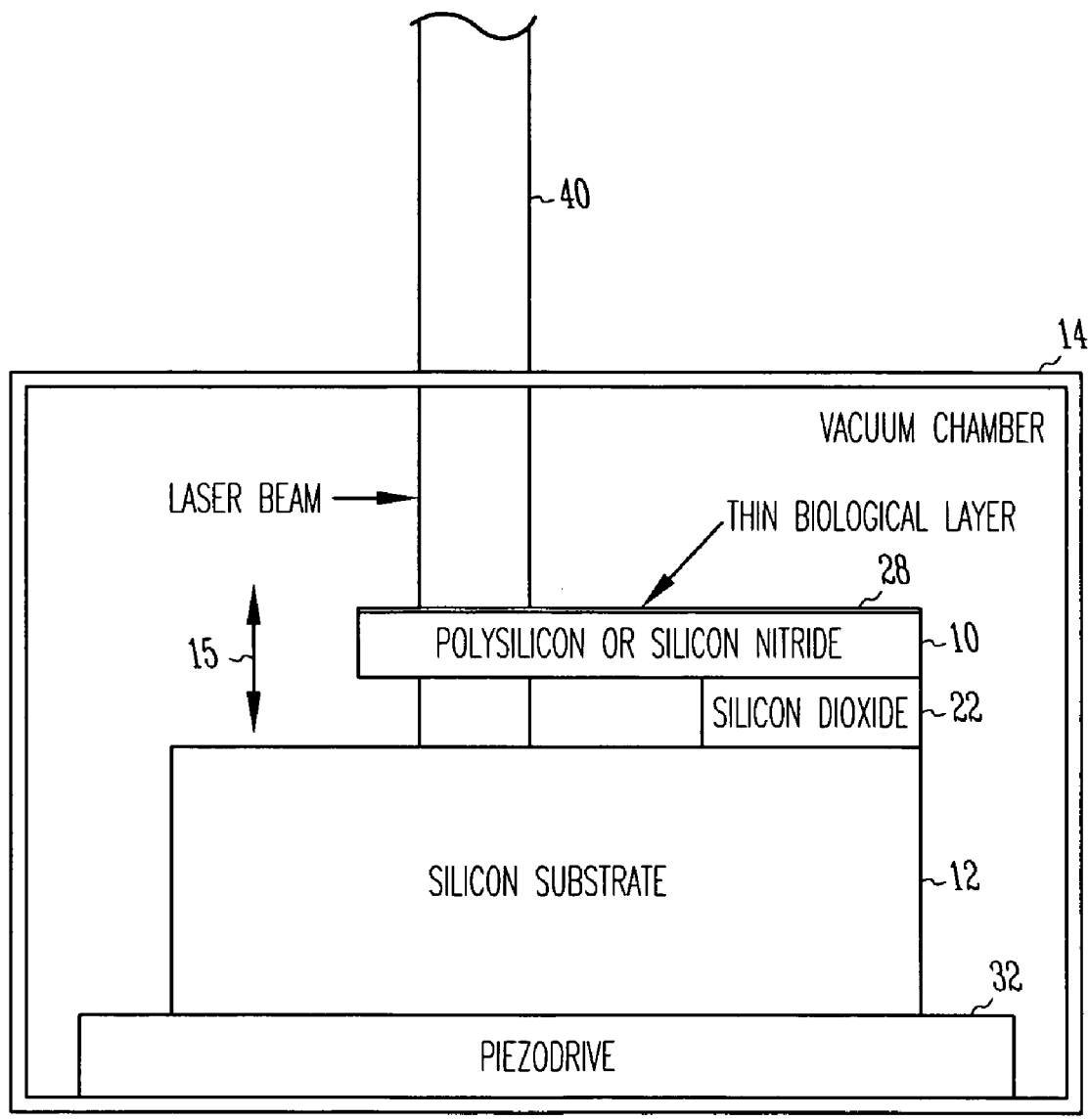
FIG. 12 illustrates a test setup for use with a beam fabricated using surface micromachining.

A profile view of the resonator is also illustrated in FIG. 12. In the example shown, substrate 12 is fabricated of silicon, beam 10 is fabricated of polysilicon and between substrate 12 and beam 10 is a layer of silicon dioxide. In this case, beam 10 is semi-transparent to the incident light. In other words, a portion of incident light is reflected by beam 10 and a portion of incident light is transmitted through beam 10. The thickness t of beam 10 is sufficiently small to render beam 10 at least partially transparent.

Optionally, a vacuum chamber, can enhance the mechanical quality factor, and thus enhance sensitivity. In FIG. 10, chamber 14 provides an evacuated environment for beam 10. The vacuum environment increases the mechanical quality factor Q, thus increasing beam 10 sensitivity and ability to detect smaller masses.

The configuration shown in FIG. 10 may be used to generate frequency response data using a single photocell. In contrast, the bulk micromachined configurations normally employs either two photodetectors or a conventional split cell photodiode. Using two photodetectors, or a split cell photodiode, the voltage differential between the two sensing elements provides the signal for driving the spectrum analyzer. The sensitivity of such a resonator is limited by the high speed capabilities of the instrumentation amplifiers coupled to the photodetectors, or split cell photodiode, and driving the spectrum analyzer. For example, the bandwidth of typical operational amplifiers, that is the 3 dB drop point, is in the range of several megahertz. This limitation of frequency response thus limits the sensitivity of the resonator.

Using a single photocell, on the other hand, the frequency response is not sensitive to a voltage differential, and thus, higher speed single-ended operational amplifiers can be utilized. In this case, the frequency responses may be in the gigahertz ranges. Thus, smaller, more sensitive, resonators may be possible. It has been demonstrated that using surface micromachined devices and single photodetectors, sensitivity can be in the range of attogram detection.

Figure 11A:
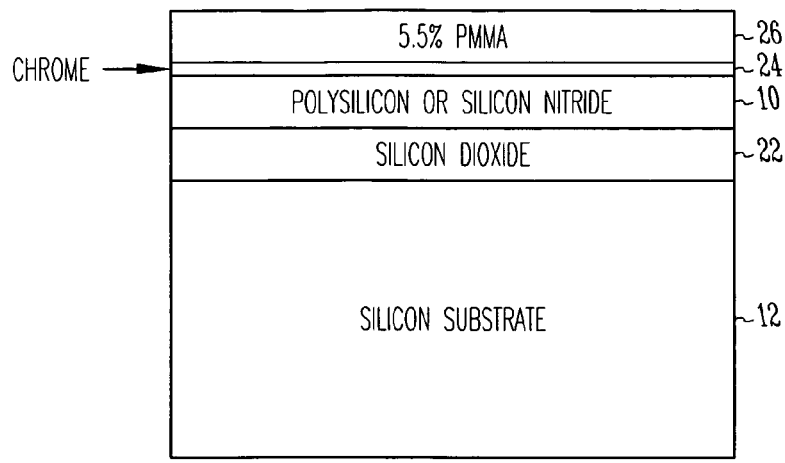
FIGS. 11A, 11B and 11C illustrate a surface micromachining fabrication process.
Figure 11B:
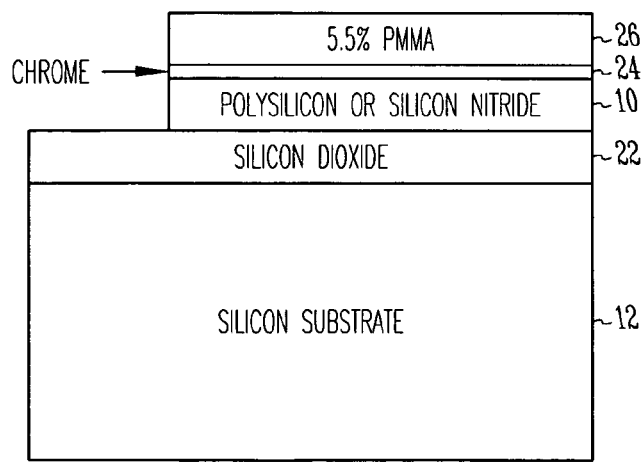
Figure 11C:
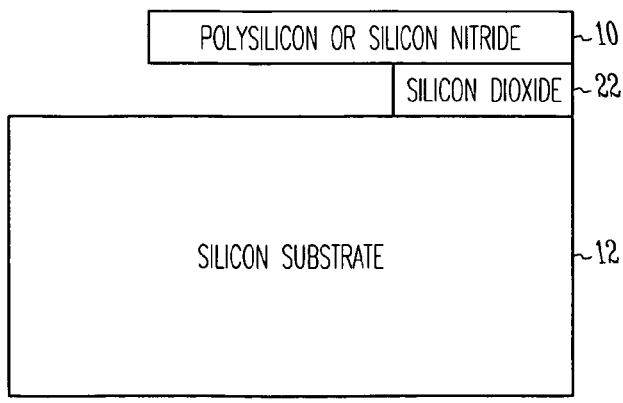

The surface micromachining fabrication process, illustrated in FIGS. 11A, 11B and 11C, begins with silicon substrate 12. With reference to FIG. 11A, an 800 nm layer of silicon dioxide, layer 22, is thermally grown on silicon substrate 12 in an atmosphere of pyrogenic steam. Undoped poly-silicon, forming beam 10, is then deposited on top of the sacrificial oxide layer 22. By way of example and not by way of limitation, silicon nitride may also be used for forming beam 10. The poly-silicon is then thermally annealed at 1050° C. to alleviate stresses from the residual film. Next, a conductive 30 nm layer of chromium, layer 24, is thermally evaporated. This conductive layer reduces charging effects in the subsequent e-beam lithographic definition of the resonating beam. Layer 26, of 5.5% polymethylmethacrylate (hereinafter "PMMA") is then spun on at 2,000 rpm for a period of 60 seconds, resulting in a layer thickness of approximately 370 nm. PMMA layer 26 is soft baked on a hotplate at 170° C. for approximately 15 minutes. FIG. 11A illustrates the results of the foregoing procedure.

PMMA layer 26 is exposed using an electron beam at a dose current of 7.5 nA and a dose of 220 µC/cm³. The wafer is developed in 1:1 methyl isobutyl ketone:isopropanol (MIBK:IPA) for 1 minute, rinsed with IPA and nitrogen ($N_2$) dried. Descumming is carried out using 14 sccm $O_2$ at a pressure of 600 mTorr and power level of 150 W for period of 1 minute. FIG. 11B illustrates a representative profile view.

FIG. 11C illustrates the result of subsequent steps. Poly-silicon is selectively removed using reactive ion etching. PMMA layer 26 is stripped using oxygen plasma and chrome (Cr) 24 is removed using a wet etch. The structure is then immersed in a solution of hydrofluoric acid which etches the exposed silicon dioxide layer 22, thereby undercutting and freeing beam 10.

FIG. 12 illustrates a test setup for use with beam 10 fabricated according to the above procedure. Piezo driver 32 is used to determine the resonant frequency of the beam when operating in a vacuum bound by vacuum chamber 14. Piezo drive 32 is helpful with small resonators since the amplitude of vibration due to ambient noise is very small (less than 0.01 nm). The cantilever is then coated with a self-assembled monolayer 28 and the resonant frequency is measured. The frequency shift is then correlated to the added mass.

Figure 13:
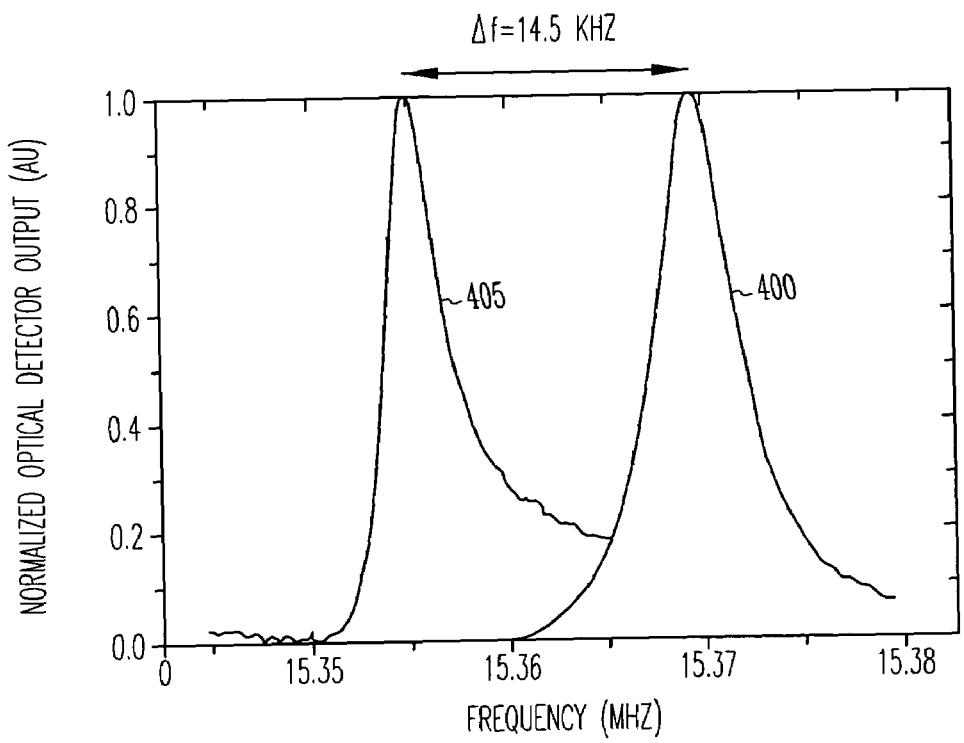
FIG. 13 illustrates frequency response of a beam operating in a vacuum.

In one embodiment, a series of beams were fabricated and a monolayer of vapor deposited hexamethyldisilazane ("HMDS") was applied. FIG. 13 illustrates the measured frequency response. In the figure, response curve 400 represents beam 10 before depositioning of the monolayer and response curve 405 represents after depositioning of the monolayer. The observed frequency shift was 14.5 kHz using beam 10 having dimensions of l=4 µm, w=2 µm, and t=340 nm. The calculated additional mass was 14.8 femtograms, and therefore, the sensitivity is approximately 1 Hz/attogram.

This sample was prepared in a following manner, first after the undercutting of the oxide with hydrofluoric acid ("HF"), the surface was devoid of any adsorbed water vapors. Sample was then placed inside a vacuum chamber and the first resonance peak was obtained. Sample was dehydrated at 150° C. for 1 hour and immediately placed into the HMDS deposition oven. Sample was then placed into the vacuum chamber and the frequency shift reported in FIG. 13 was observed.

Figure 14:
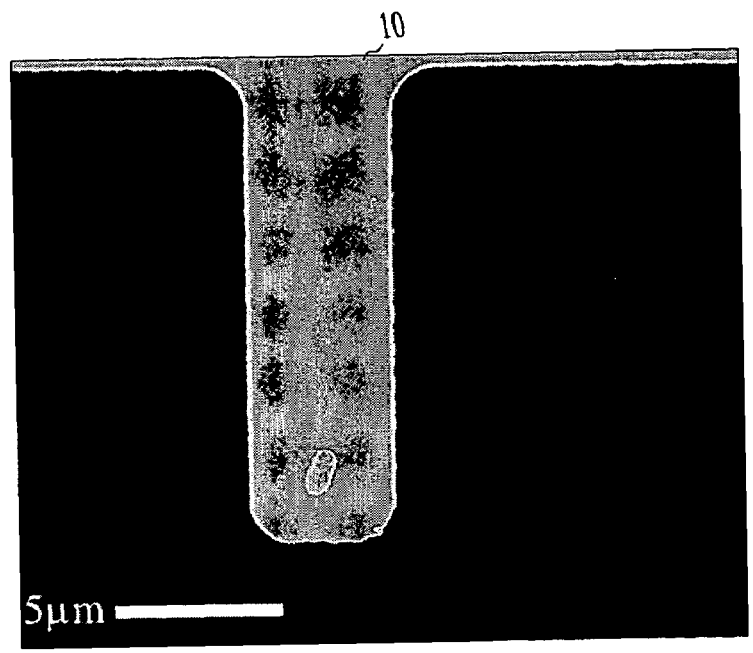
FIG. 14 illustrates a scanning electron micrograph of a single cell bound to an immobilized antibody layer on the surface of a beam.
Figure 15:
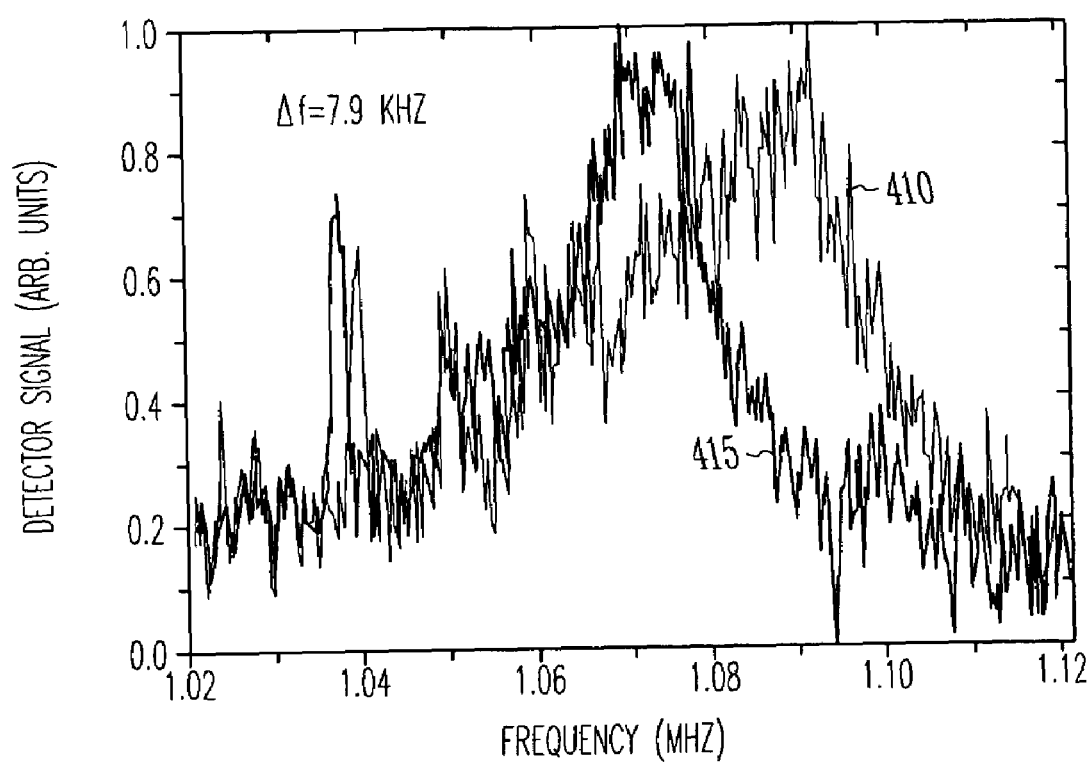
FIG. 15 illustrates the corresponding frequency response using the beam of FIG. 14.

FIG. 14 illustrates a scanning electron micrograph of a single cell bound to the immobilized antibody layer on the surface of beam 10. Beam 10 had dimensions of l=15 µm, w=5 µm, and t=320 nm. A thin layer, under 10 nm, of Au/Pd was evaporated onto beam 10 to reduce charging effects during SEM imaging. FIG. 14 illustrates the corresponding frequency response measured before and after the placement of the cell on beam 10. The frequency response measurements of FIG. 15 were made under ambient conditions using the optical deflection setup. The response curves illustrate thermal and ambient noise spectra due to the transverse vibrations of beam 10. Curve 410 illustrates the response before cell attachment and curve 415 illustrates the response after cell attachment.

Figure 16A:
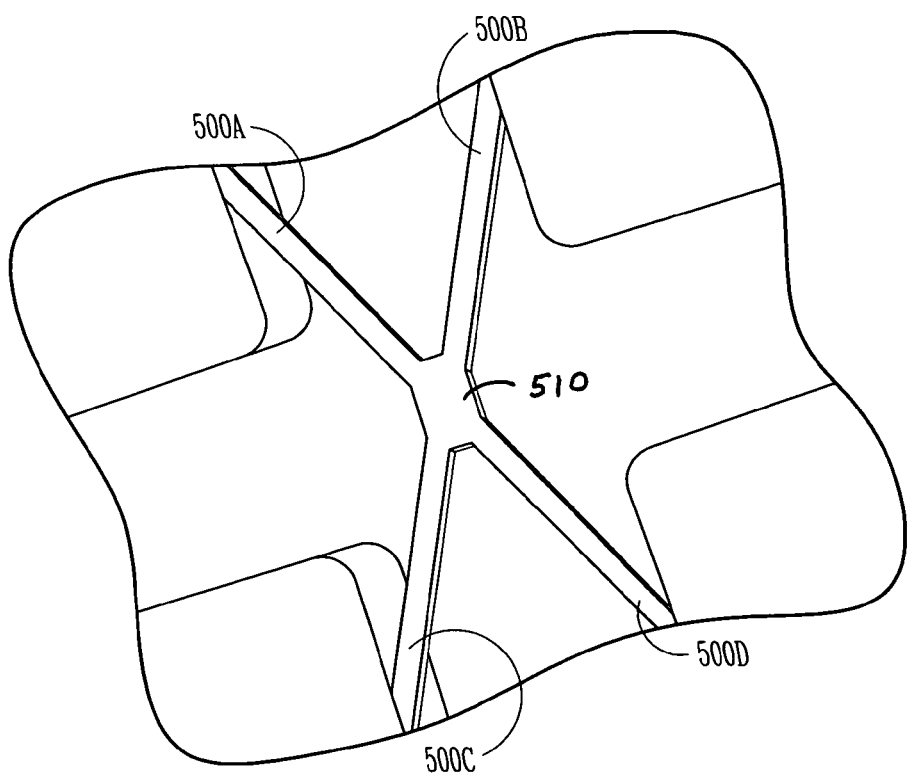
FIGS. 16A, 16B, 16C and 16D illustrate alternative configurations for a resonant sensor pursuant to the present system.
Figure 16B:
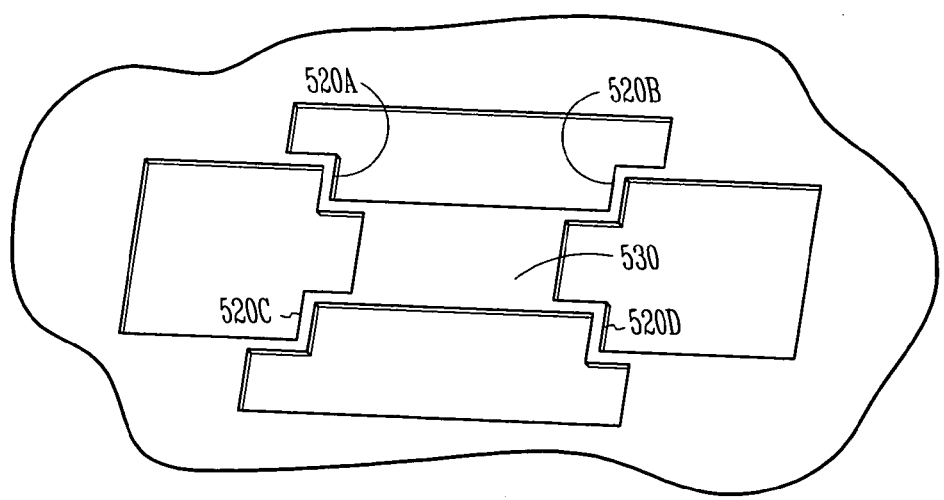
Figure 16C:
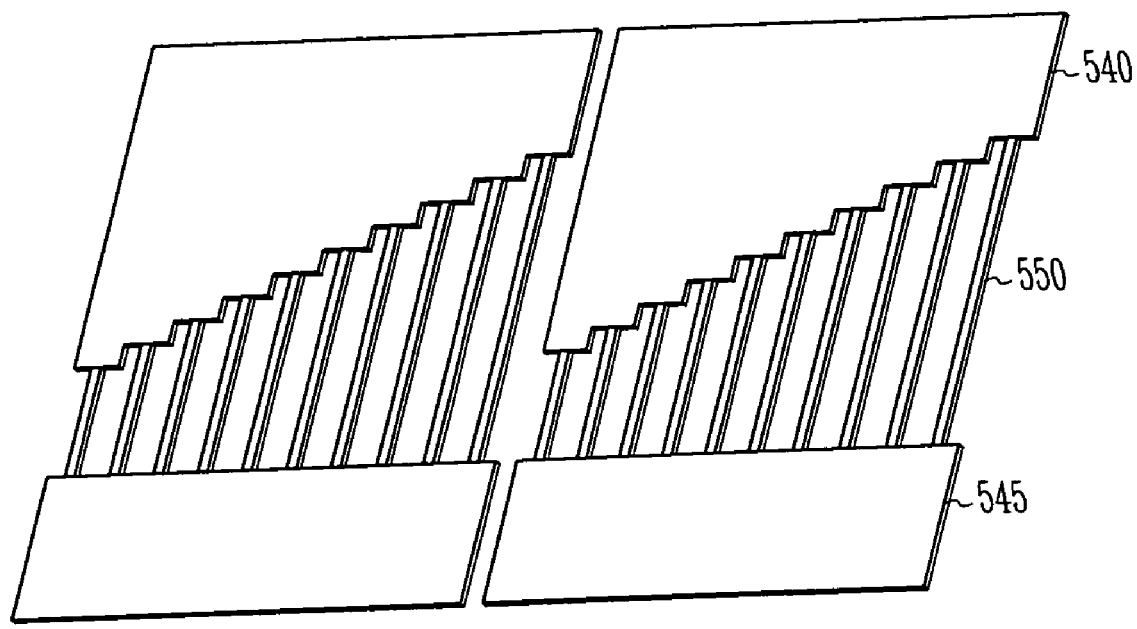
Figure 16D:
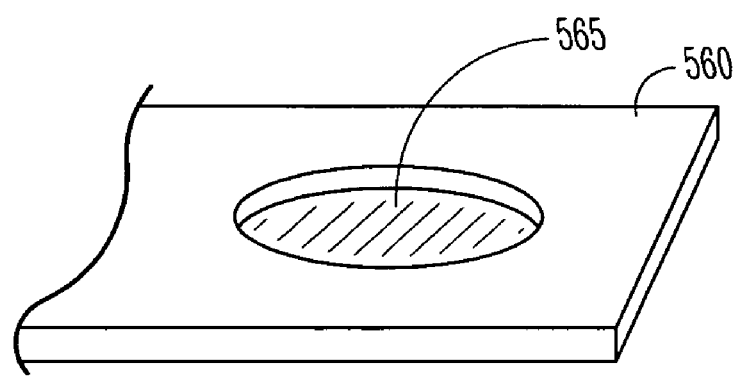

Various structures may be used to detect mass differences pursuant to the present system. For example, FIGS. 16A, 16B, 16C and 16D illustrate alternative suitable structures. In FIG. 16A, the structure includes four linear members 500A, 500B, 500C and 500D extending radially from center element 510. In one embodiment as illustrated in FIG. 16A, center element 510 is approximately 1 µm in length and linear members 500A, 500B, 500C and 500D are 200 nm thick and 150 nm in width. Linear members 500A, 500B, 500C and 500D are immobilized at one end by attachment to external structure. The inner ends of the four linear members support center element 510 which is free to resonate in an out of plane mode. The resonant frequency of the structure can be determined by optical means operating on light reflected, or refracted, from center element 510. FIG. 16B illustrates another embodiment also having a resonating center element and four supporting linear members. Center element 530 in FIG. 16B is approximately 4 µm in length. In FIG. 16B, linear elements 520A, 520B, 520C and 520D include orthogonal portions. In FIG. 16C, two arrays of linear members, or strings, are illustrated. String 550 is a representative string and is immobilized by attachment to structure 540 and 545. In the figure, the width of the strings shown in the left array is 200 nm and those of the right array are 120 nm, and for each, the thickness is 50 nm. In the figure, the length of the strings range between 7 µm and 16 µm. In FIG. 16D, a drum-shaped, or disk-shaped, structure is illustrated. The center of drum 565 is unsupported and the perimeter of drum 565 is supported by external structure 560. Optical detection means can be used to detect resonance of the drum structure. Alternatively, the center of the drum may be immobilized and the perimeter free to resonate. Other structures and other dimensions may be employed to yield a structure having a desired sensitivity to mass differentials at a particular resonant frequency. Structures other than cantilever beams can be used for detecting mass differentials as herein described.

CONCLUSION

Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention.

What is claimed is:

1. A system for detecting an analyte, the system comprising:
    a light source;
    a resonant structure and an underlying substrate positioned under said structure to form a gap therebetween, said structure has an immobilized binding partner that binds to said analyte on a surface of said resonant structure, wherein said structure resonates under ambient conditions at a frequency based on the mass of said analyte; and
    a photodetector responsive to light reflected by said resonant structure and light reflected by said substrate, wherein a first portion of said light is reflected by said surface of said resonant structure and a second portion of said light passes through said resonant structure and said gap and is reflected by said underlying substrate, wherein said photodetector provides an output corresponding to a resonant frequency shift of said structure, said shift corresponding to a change in said mass of said analyte.

2. The system of claim 1 further comprising a processor coupled to said photodetector for determining the mass of said analyte.

3. The system of claim 1 further comprising a spectrum analyzer coupled to said photodetector for determining a resonant frequency of said structure.

4. The system of claim 1 where said photodetector comprises a first photodiode and a second photodiode.

5. The system of claim 1 wherein said photodetector is adapted for generating a differential voltage signal.

6. The system of claim 1 wherein said structure comprises silicon, silicon nitride, silicon dioxide, silicon carbide, polysilicon, carbon, diamond-like carbon film, metal or gallium arsenide.

7. The system of claim 1 wherein said resonant structure is coupled to a support.

8. The system of claim 1 wherein said structure is adapted for vibrating under ambient conditions including thermal noise.

9. The system of claim 1 wherein said structure is adapted for vibrating under ambient conditions including ambient air vibrations.

10. The system of claim 1 wherein said structure is coupled to a piezoelectric drive.

11. The system of claim 1 further comprising a vacuum environment in which said structure operates.

12. The system of claim 1 wherein the analyte is a pathogen.

13. The system of claim 1 wherein the analyte is a microorganism.

14. The system of claim 1 wherein the analyte is a bacteria, a virus or a subunit thereof.

15. The system of claim 1 wherein the binding partner for the analyte is an antibody that binds to said analyte.

16. The system of claim 1 wherein the binding partner is a cellular receptor that binds to a ligand.

17. The system of claim 1 wherein the analyte is a ligand specific for a cellular receptor.

18. The system of claim 1 wherein the analyte is a metallic ion and the binding partner is a chelator that binds said metallic ion.

19. The system of claim 1 wherein the binding partner includes a DNA sequence.

20. The system of claim 1 wherein said structure comprises a cantilever beam.

21. The system of claim 20 wherein said cantilever beam vibrates in an out of plane mode.

22. The system of claim 20 wherein said cantilever beam has a length of 0.5 to 1000 μm.

23. The system of claim 1 wherein the photodetector is responsive to interference based on the light reflected by said resonant structure and light reflected by the substrate.

* * * * *